United States Patent
Ono et al.

(10) Patent No.: US 9,872,661 B2
(45) Date of Patent: Jan. 23, 2018

(54) X-RAY CT APPARATUS, AND IMAGE PROCESSING APPARATUS

(71) Applicant: TOSHIBA MEDICAL SYSTEMS CORPORATION, Otawara-Shi (JP)

(72) Inventors: Toshiyuki Ono, Kawasaki (JP); Takashi Ida, Kawasaki (JP); Shuhei Nitta, Ota (JP); Hiroaki Nakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 128 days.

(21) Appl. No.: 14/944,745

(22) Filed: Nov. 18, 2015

(65) Prior Publication Data
US 2016/0135774 A1    May 19, 2016

(30) Foreign Application Priority Data

Nov. 19, 2014   (JP) .................................. 2014-234946
Nov. 12, 2015   (JP) .................................. 2015-222352

(51) Int. Cl.
*A61B 6/00*   (2006.01)
*A61B 6/03*   (2006.01)
*G06T 11/00*   (2006.01)

(52) U.S. Cl.
CPC ............ *A61B 6/5205* (2013.01); *A61B 6/032* (2013.01); *A61B 6/4241* (2013.01);
(Continued)

(58) Field of Classification Search
CPC .................. G06T 11/003; G06T 11/005; G06T 2207/10081; A61B 6/032; A61B 6/5205; A61B 6/5258
See application file for complete search history.

(56) References Cited

U.S. PATENT DOCUMENTS

| 5,416,815 A | 5/1995 | Hsieh ................................ 378/4 |
| 7,558,362 B2 | 7/2009 | Shechter et al. .................. 378/4 |

(Continued)

FOREIGN PATENT DOCUMENTS

| JP | 7-136157 A | 5/1995 |
| JP | 2008-505676 A | 2/2008 |

(Continued)

OTHER PUBLICATIONS

Huanjun Ding et al., "Image-Based Spectral Distortion Correction for Photon-Counting X-ray Detectors", Medical physics, 39 (4), Apr. 2012, pp. 1864-1876.

*Primary Examiner* — Andrew W Johns
(74) *Attorney, Agent, or Firm* — Oblon, McClelland, Maier & Neustadt, L.L.P.

(57) ABSTRACT

According to an embodiment, an X-ray computed tomography apparatus includes processing circuitry. The processing circuitry is configured to acquire first projection data that is based on a first spectrum representing an amount of radioactive rays in a unit of energy of the radioactive rays having passed through a subject and detected by a detector. The processing circuitry is configured to generate second projection data by correcting the first projection data based on a response characteristic of the detector. The processing circuitry is configured to operate reconstruction process to the second projection data.

19 Claims, 10 Drawing Sheets

(52) U.S. Cl.
CPC ............ *G06T 11/005* (2013.01); *A61B 6/481* (2013.01); *A61B 6/482* (2013.01); *G06T 2211/408* (2013.01)

(56) References Cited

U.S. PATENT DOCUMENTS

| | | | |
|---|---|---|---|
| 8,585,286 B2 | 11/2013 | Livne et al. | 378/207 |
| 2007/0297562 A1* | 12/2007 | Konno et al. | 378/12 |
| 2014/0105370 A1 | 4/2014 | Yamakawa et al. | A61B 6/585 |
| 2015/0287221 A1* | 10/2015 | Takayama et al. | G06T 11/003 382/131 |
| 2015/0348289 A1 | 12/2015 | Ida et al. | G06T 11/003 |
| 2016/0054453 A1 | 2/2016 | Moriyasu et al. | G01T 1/17 |
| 2016/0058404 A1 | 3/2016 | Nitta et al. | A61B 6/482 |
| 2016/0242720 A1 | 8/2016 | Ida et al. | A61B 6/5205 |

FOREIGN PATENT DOCUMENTS

| | | |
|---|---|---|
| JP | 2011-516852 A | 5/2011 |
| JP | 2015-198833 A | 11/2015 |
| JP | 2016-10676 A | 1/2016 |
| JP | 2016-52349 A | 4/2016 |
| JP | 2016-55157 A | 4/2016 |
| JP | 2016-59509 A | 4/2016 |
| JP | 2016-154839 A | 9/2016 |
| WO | WO 2012/144589 A1 | 10/2012 |

\* cited by examiner

FIG.12
(a)
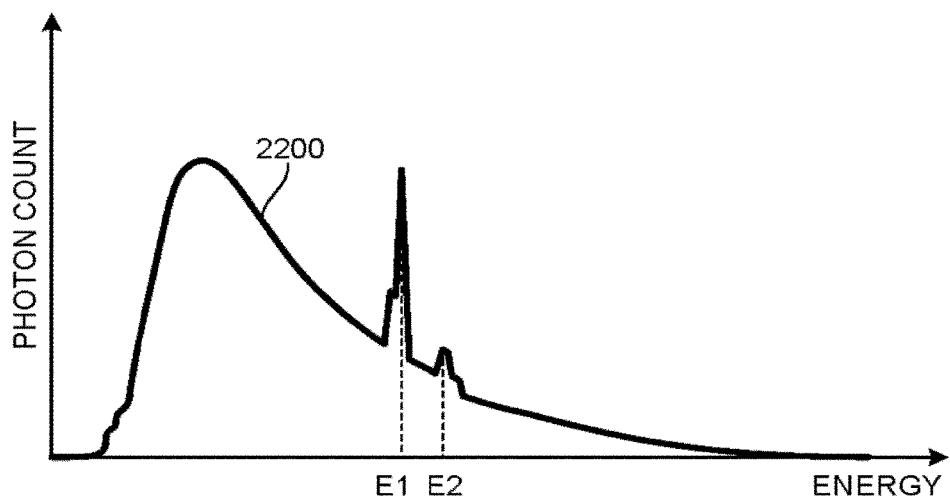
(b)
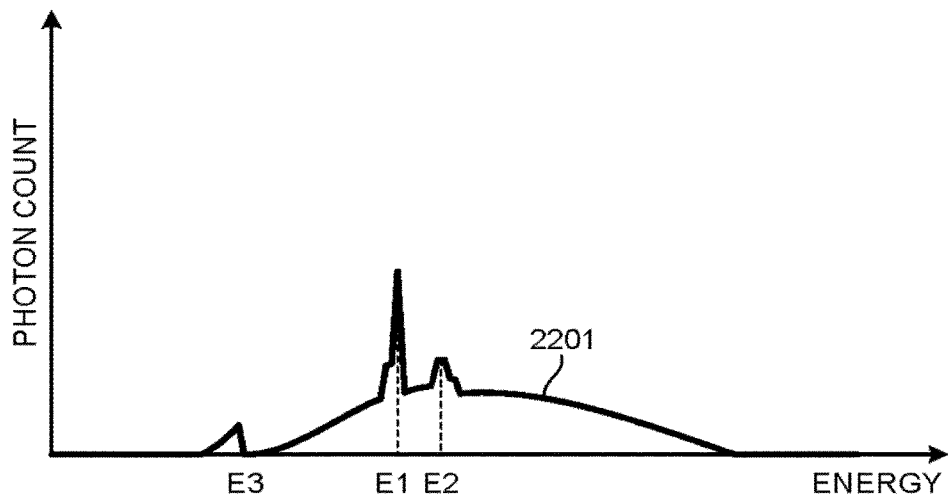

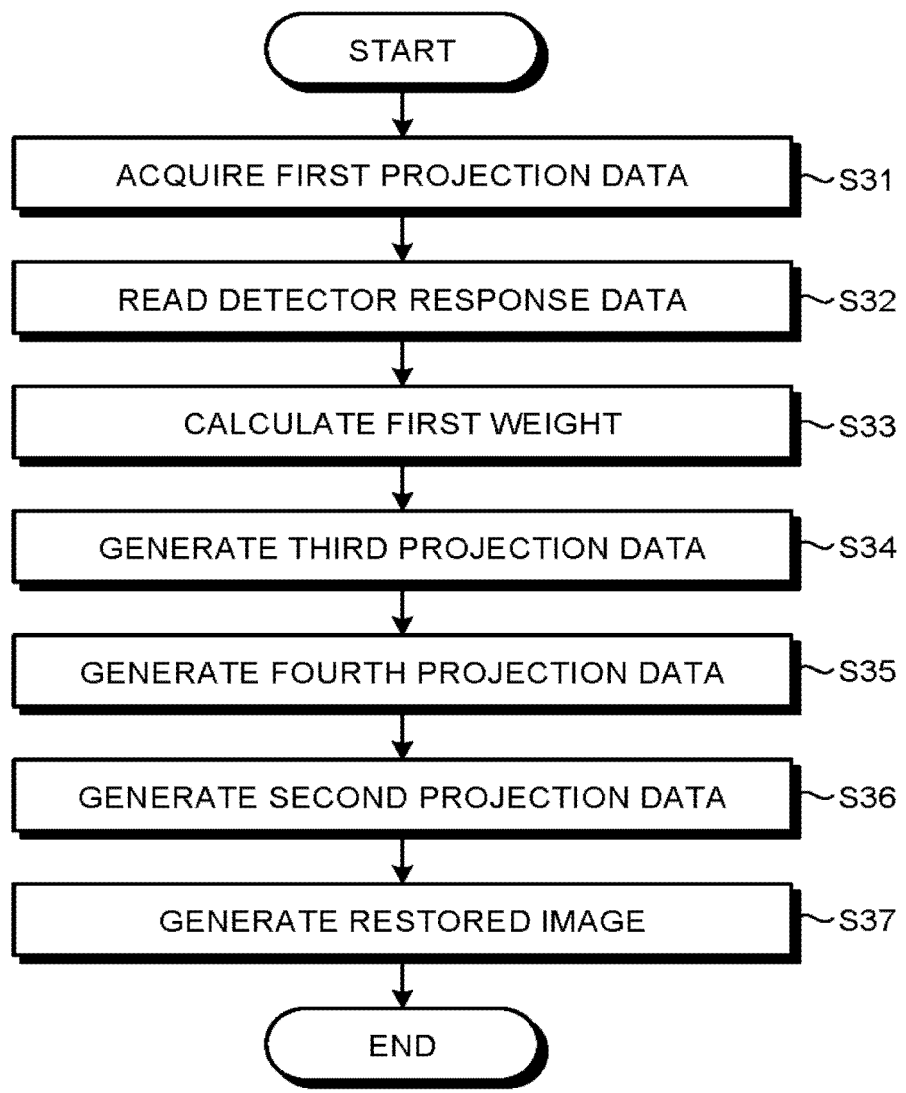

X-RAY CT APPARATUS, AND IMAGE PROCESSING APPARATUS

CROSS-REFERENCE TO RELATED APPLICATIONS

This application is based upon and claims the benefit of priority from Japanese Patent Application No. 2014-234946, filed on Nov. 19, 2014; and Japanese Patent Application No. 2015-222352, filed on Nov. 12, 2015, the entire contents of which are incorporated herein by reference.

FIELD

Embodiments described herein relate generally to an X-ray computed tomography (CT) apparatus, an image processing apparatus, and a computer program product.

BACKGROUND

Silicon-based photomultipliers are now being developed actively, and development of radiation detectors such as X-ray CT apparatuses using a photomultiplier is also advancing. An example of such an X-ray CT apparatus is a spectral CT apparatus or a photon-counting CT apparatus that detects a spectrum of photon counts in respective units of X-ray energy passed through a subject. X-ray CT apparatuses such as a photon-counting CT apparatus reconstruct a restored image representing linear attenuation coefficients of a subject, based on the degree of attenuation in the spectrum of the X-rays passed through the subject.

A spectrum of X-rays observed by the detector is distorted with respect to a spectrum of the X-rays incident on the detector, due to a fluctuation introduced in a process of converting X-ray energy into observation values, X-ray energy deviation due to noise, or interactions of X-rays with the detector elements, e.g., photoelectric conversion or scattering. The linear attenuation coefficients of a subject calculated based on such a distorted spectrum are therefore not exactly the true values.

Disclosed as an X-ray spectrum detection method for correcting such a distorted spectrum is a technology for acquiring actual X-ray photon count measurements using a subject specialized for calibration, acquiring theoretical values from a simulation, and for acquiring a correction formula for bringing the actual measurements closer to the theoretical values representative of the respective energy units. The correction formula is then applied to a detected X-ray spectrum.

The technology that applies a correction formula, however, is incapable of correcting the photon counts accurately when the subject has a composition different from the condition under which the correction formula is created. In such a case, the pixel values of a sinogram acquired from a spectrum of X-rays passed through the subject may be different from the true values.

BRIEF DESCRIPTION OF THE DRAWINGS

FIG. 12 illustrates an exemplary outgoing spectrum, and an exemplary subject spectrum;

FIG. 16 is a flowchart illustrating an exemplary operation of the image processor according to the third embodiment.

DETAILED DESCRIPTION

Figure 1:
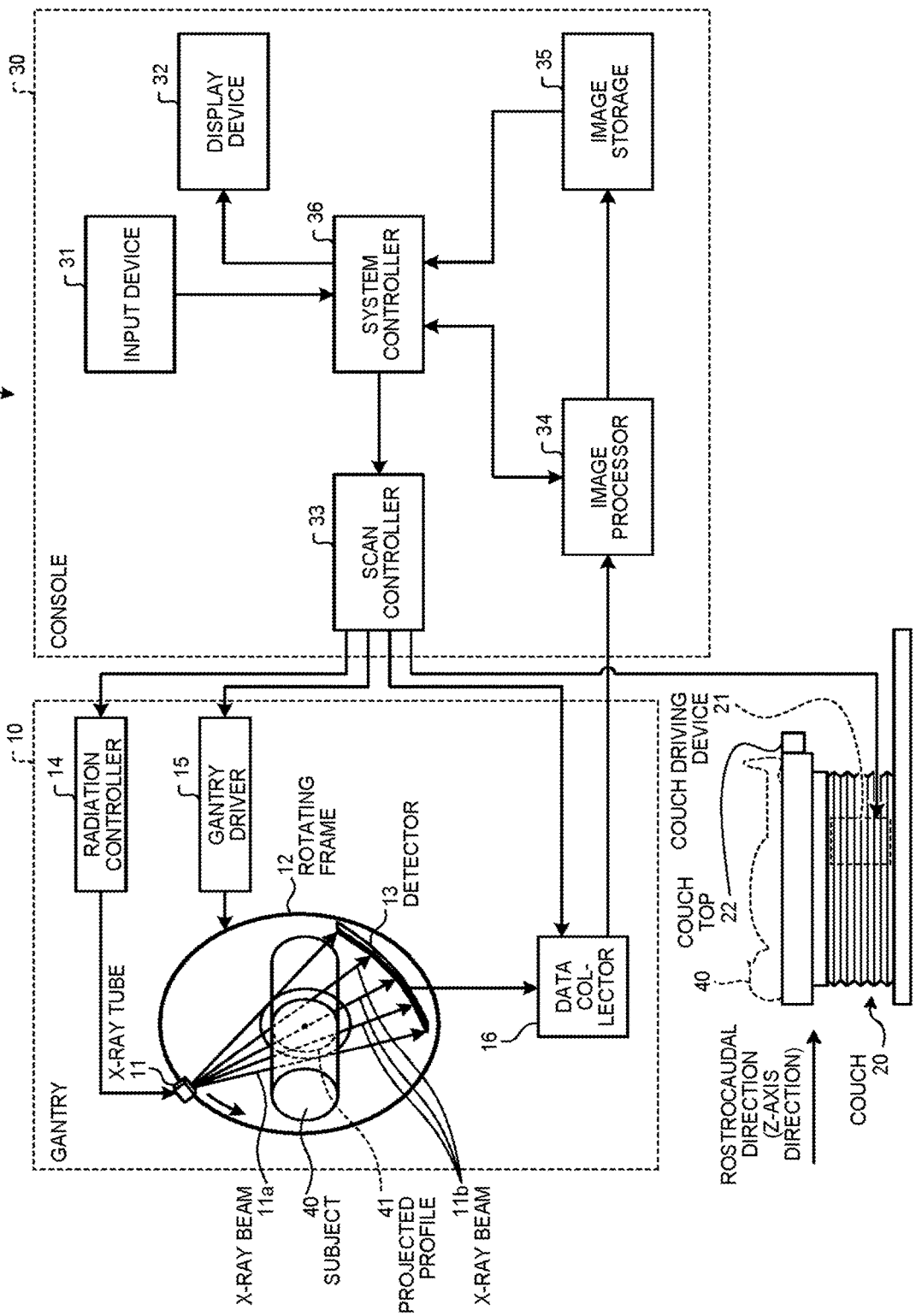
FIG. 1 is a block diagram of an X-ray examination apparatus according to a first embodiment.

According to an embodiment, an X-ray computed tomography apparatus includes processing circuitry. The processing circuitry is configured to acquire first projection data that is based on a first spectrum representing an amount of radioactive rays in a unit of energy of the radioactive rays having passed through a subject and detected by a detector. The processing circuitry is configured to generate second projection data by correcting the first projection data based on a response characteristic of the detector. The processing circuitry is configured to operate reconstruction process to the second projection data.

An X-ray CT apparatus and an image processing apparatus according to some embodiments will now be explained in detail with reference to some drawings. In the drawings mentioned below, the same parts are assigned with the same reference numerals. Specific configurations, however, should be understood along with the following descriptions, because the drawings are merely schematic representations.

First Embodiment

FIG. 1 is a schematic of an overall configuration of an X-ray examination apparatus according to a first embodiment. The overall configuration of this X-ray examination apparatus 1 will now be generally explained with reference to FIG. 1.

The X-ray examination apparatus 1 that is an example of an X-ray CT apparatus is a spectral CT apparatus or a photon-counting CT apparatus, for example, that acquires a tomographic image of a projected profile 41 of a subject 40, by passing X-rays that are exemplary radioactive rays through a subject 40, and by detecting the X-ray energy as a spectrum of photon counts in units of the energy, as illustrated in FIG. 1. The X-ray examination apparatus 1 includes a gantry 10, a couch 20, and a console 30 (image processing apparatus), as illustrated in FIG. 1.

The gantry 10 is a device that emits and passes X-rays to and through the subject 40, and detects the spectrum. The gantry 10 includes an X-ray tube 11, a rotating frame 12, a detector 13, a radiation controller 14, a gantry driver 15, and a data collector 16.

The X-ray tube 11 is a vacuum tube that generates an X-ray by receiving a supply of high voltage from the radiation controller 14, and irradiates the subject 40 with an X-ray beam 11a. The spectrum of photon counts in units of energy of the X-ray energy emitted from the X-ray tube 11 is determined based on the tube voltage and the tube current of the X-ray tube 11, and the type of a target used in the radiation source (e.g., tungsten). The energy of the X-ray output from the X-ray tube 11 attenuates as the X-ray passes through the subject 40, by a degree dependent on the conditions of the substances making up the subject 40, causing the photon count of the corresponding energy band to decrease, and the spectrum to change.

The rotating frame 12 is a ring-shaped support that supports the X-ray tube 11 and the detector 13 in a manner facing each other across the subject 40.

Figure 4:
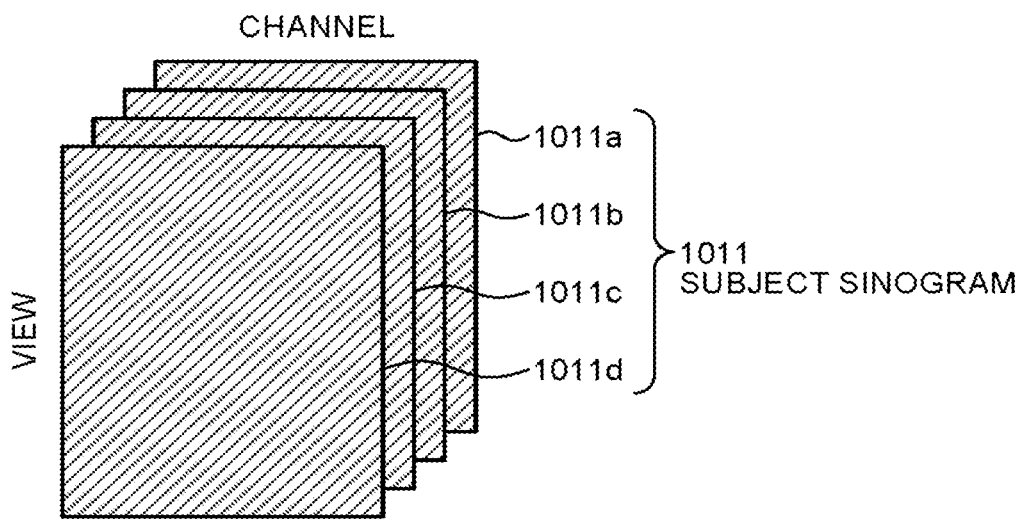
FIG. 4 is a schematic illustrating exemplary subject sinograms.

The detector 13 is a detector that detects a photon count in each unit of the energy of the X-ray beam 11b that is the X-ray emitted from the X-ray tube 11 and passed through the subject 40. In other words, the detector 13 detects a spectrum represented as photon counts of the X-ray energy at each channels, as illustrated in FIG. 4 which is described later. Hereinafter, the spectrum detected by the detector 13 is sometimes referred to as a "detected spectrum". The detector 13 detects a spectrum at each view, while the detector 13 is rotated in the circumferential direction of the rotating frame 12, as illustrated in FIG. 1. A view herein means an increment of a predetermined angle at which the detector 13 detects a spectrum, across the 360 degrees corresponding to one rotation along the circumferential direction of the rotating frame 12. In other words, in a configuration in which the detector 13 detects a spectrum at an increment of 0.5 degree, one view=0.5 degree. The detector 13 is a two-dimensional array detector in which a plurality of detecting elements arranged along the channel direction (the circumferential direction of the rotating frame 12) are also arranged in plurality along the rostrocaudal direction (slice direction) of the subject 40 (the Z-axis direction illustrated in FIG. 1). The array of detecting elements in the detector 13 may include photon-counting detecting elements as well as integration detecting elements. Furthermore, the pair of the X-ray tube 11 and the detector 13 may be provided in plurality.

The radiation controller 14 is a device for generating high voltage and supplying the generated high voltage to the X-ray tube 11.

The gantry driver 15 is a device for driving the X-ray tube 11 and the detector 13 to rotate in the circular path around the subject 40, by driving the rotating frame 12 to rotate. The gantry driver 15 is not limited to a structure that drives both of the X-ray tube 11 and the detector 13 in rotation. For example, the detector 13 may be configured to include an array of detecting elements provided along the entire circumferential direction of the rotating frame 12, and the gantry driver 15 may be configured to drive only the X-ray tube 11 in rotation.

The data collector 16 is a device for collecting data of a spectrum (first spectrum) of photon counts in units of the energy detected at each channel of the detector 13. The data collector 16 then applies processes such as amplification and analog-to-digital (A/D) conversion to each piece of collected spectrum data, and generates sinograms corresponding to respective ranges of energy having a predetermined width (hereinafter, sometimes simply referred to as "units of the energy"), and outputs the sinograms to the console 30.

The couch 20 is a device on which the subject 40 is laid, and includes a couch driving device 21 and a couch top 22, as illustrated in FIG. 1.

The couch top 22 is a couch such as a bed on which the subject 40 is laid. The couch driving device 21 is a device that moves the subject 40 into the rotating frame 12 by moving the couch top 22 along the rostrocaudal direction of the subject 40 laid on the couch top 22 (Z-axis direction).

The console 30 is a device that receives operator operations from the X-ray examination apparatus 1, and reconstructs a tomographic image (restored image) from the data collected by the gantry 10. The console 30 includes an input device 31 (input unit), a display device 32, a scan controller 33, an image processor 34, an image storage 35, and a system controller 36, as illustrated in FIG. 1.

The input device 31 is a device for allowing an operator operating the X-ray examination apparatus 1 to input various commands through operations, and transmitting the various commands input by operations to the system controller 36. Examples of the input device 31 include a mouse, a keyboard, buttons, a trackball, and a joystick.

The display device 32 is a device for displaying a graphical user interface (GUI) for receiving operation commands from the operator via the input device 31, and a restored image (tomographic image) stored in the image storage 35, which will be described later. The display device 32 is, for example, a cathode ray tube (CRT) display, a liquid crystal display (LCD), or an organic electro-luminescence (EL) display.

The scan controller 33 is a processing unit that controls the operations of the radiation controller 14, the gantry driver 15, the data collector 16, and the couch driving device 21. Specifically, the scan controller 33 performs X-ray scan by causing the X-ray tube 11 to emit X-rays continuously or intermittently while the rotating frame 12 is rotated. The scan controller 33 performs, for example, helical scan in which images are captured by rotating the rotating frame 12 continuously while moving the couch top 22, and non-helical scan in which one image is captured by rotating the rotating frame 12 once around the subject 40, and in which another image is captured by rotating the rotating frame 12 once more after the couch top 22 on which the subject 40 is laid is moved by some distance.

The image processor 34 is a processing unit that reconstructs a tomographic image of the subject from the sinograms received from the data collector 16. A block diagram and an operation of the image processor 34 will be described in detail later.

The image storage 35 is a functional unit that stores therein a tomographic image (restored image) generated by the reconstruction performed by the image processor 34. The image storage 35 is a storage such as a hard disk drive (HDD), a solid state drive (SSD), and an optical disk.

The system controller 36 is a processing unit that controls the entire X-ray examination apparatus 1 by controlling the operations of the gantry 10, the couch 20, and the console 30. Specifically, the system controller 36 controls the scan controller 33 to control the gantry 10 and the couch 20 to perform the operation of collecting spectrum data from the subject 40. The system controller 36 also controls the image processor 34 to control the tomographic image reconstructing process. The system controller 36 also reads a tomographic image from the image storage 35, and displays the tomographic image on the display device 32.

Explained herein is an example in which the data collector 16 generates sinograms, in units of a predetermined energy band, from the spectrum data collected by the data collector 16, but embodiments are not limited thereto. In other words, the data collector 16 may transmit the collected spectrum data to the image processor 34, and cause image processor 34 to generate sinograms in units of an energy band having a predetermined width from the spectrum data.

Figure 2:
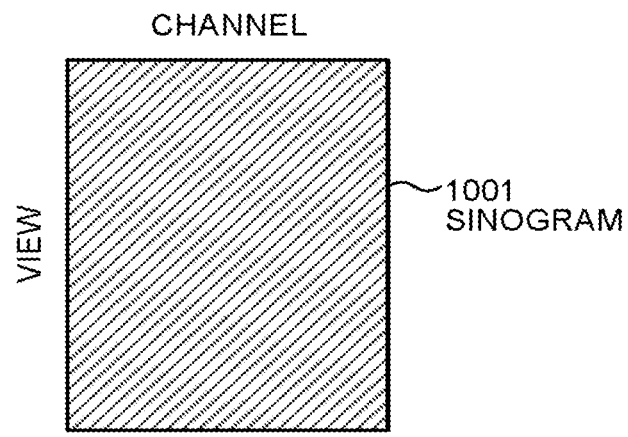
FIG. 2 is a schematic for explaining a sinogram.
Figure 3:
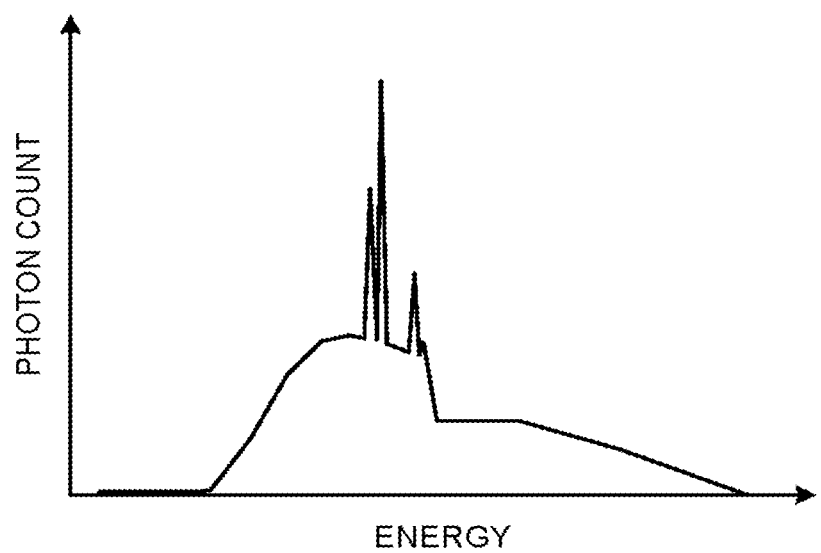
FIG. 3 is a schematic illustrating an example of a spectrum of energy detected at a specific channel.
Figure 5:
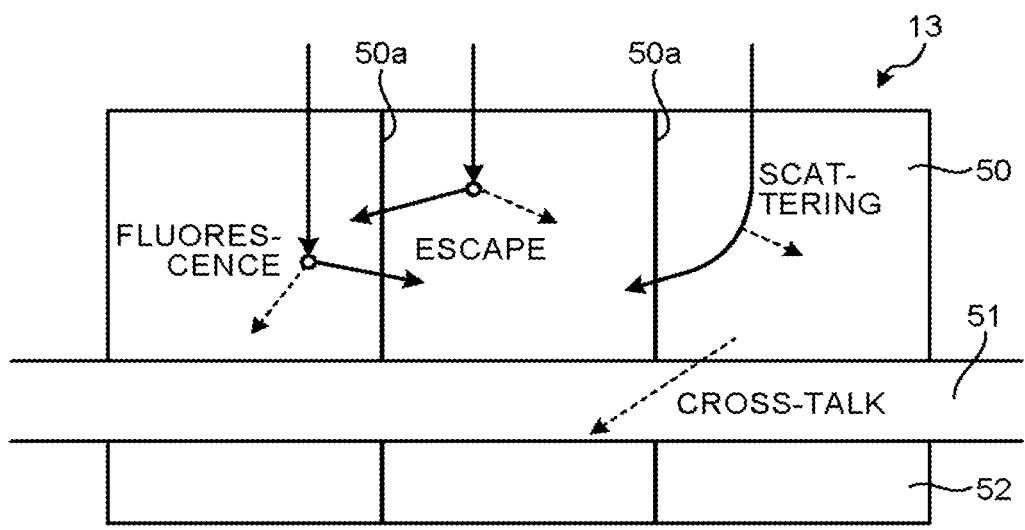
FIG. 5 is a schematic for explaining physical phenomena related to X-rays that are incident on the detector.
Figure 6:
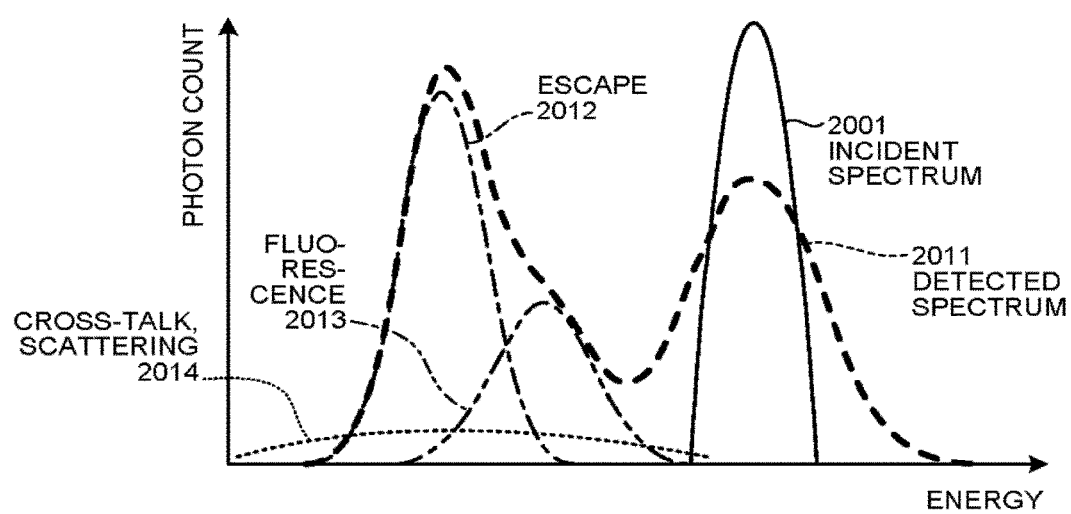
FIG. 6 is a schematic for explaining a detected spectrum.

FIG. 2 is a schematic for explaining a sinogram. FIG. 3 is a schematic illustrating an example of the spectrum of the energy detected at a specific channel of the detector. FIG. 4 is a schematic illustrating exemplary subject sinograms. FIG. 5 is a schematic for explaining physical phenomena related to X-rays that are incident on the detector. FIG. 6 is a schematic for explaining a detected spectrum. A sinogram, an X-ray energy spectrum, and a detected spectrum and the like detected by the detector 13 will now be explained with reference to FIGS. 2 to 6.

The data collector 16 in the gantry 10 generates a sinogram from a spectrum (detected spectrum) of the photon counts in units of the energy detected by the detector 13, as illustrated in FIG. 3. A sinogram is a piece of data consisting of arrangement of measurements that are measured at each view of the X-ray tube 11 and at each channel of the detector 13, as in the sinogram 1001 illustrated in FIG. 2. In the explanation below, a sinogram is handled as an image in which a measurement at one view and at one channel is represented as a pixel value. Hereinafter, a sinogram generated from a spectrum of X-rays (see FIG. 3) emitted from the X-ray tube 11, passed through the subject 40, and detected by the detector 13 is referred to as a subject sinogram. A sinogram generated from a spectrum of X-rays passed through only the air, without passing through the subject 40, and detected by the detector 13 is referred to as an air sinogram. A pixel value in a subject sinogram or an air sinogram represents a photon count detected as a measurement of the detector 13, for example.

Because the detector 13 detects a spectrum of photon counts in units of the energy at each view and each channel, the X-ray scan corresponding to one rotation of the X-ray tube 11 permits the data collector 16 to acquire a subject sinogram 1011 illustrated in FIG. 4 for each of the units of the energy. In the example illustrated in FIG. 4, the spectrum is divided into four energy bands, and four subject sinograms 1011a to 1011d are acquired for the respective energy bands. In the example illustrated in FIG. 4, the spectrum is divided into four energy bands, but the number into which the spectrum is divided is not limited to four. There may be cases in which it is preferable to reconstruct images or to estimate substance densities using energy bands having uniform photon counts, from the view of improving the signal-to-noise (S/N) ratio of a restored image (an image representing the attenuation coefficients) and a density image which will be described later. This object can be achieved by the following two approaches, as an example.

First Approach: To divide the spectrum into energy bands in such a manner that the photon counts of the resultant respective energy bands are uniform at the stage of creating first projection data, which will be described later.

Second Approach: To divide the spectrum into small units (e.g., in units of 1 [keV]), and to take the sum of the photon counts, at the stage of reconstructing an image or estimating the density of a substance.

The spectrum may be divided based on an air sinogram, because the form of the spectrum is different among the pixels in a subject sinogram.

Physical phenomena that the X-rays incident on the detector 13 go through will now be explained with reference to FIG. 5. As illustrated in FIG. 5, it is assumed herein that the detector 13 is what is called an indirect conversion detector including a scintillator 50, an adhesive layer 51, and silicon photomultipliers (SiPMs) 52.

The scintillator 50 is a member that converts the incident X-ray beam 11b (see FIG. 1) into an electromagnetic wave (hereinafter, referred to as scintillation light) including at least one of an ultraviolet ray, a visible light ray, and an infrared ray having a wavelength longer than that of X-ray. The scintillator 50 is a plate member that is partitioned into a matrix-like shape in the circumferential direction of the rotating frame 12 and the slice direction, by the reflectors 50a. The reflectors 50a have a property that passes X-rays but reflects scintillation light.

The adhesive layer 51 is a layer with which the outgoing surface of the scintillators 50 adheres to the incident surface of the SiPMs 52.

The SiPM 52 is a photoelectric transducer in which a plurality of pairs of a serially connected avalanche photodiode (APD) and quench resistance are connected in parallel. When the scintillation light converted from the X-ray by the scintillator 50 passes through the adhesive layer 51, and the scintillation light becomes incident on the SiPM 52, the SiPM 52 converts the scintillation light photoelectrically into a current. The part of the SiPM 52 facing a cell that is a segment of the scintillator 50 partitioned by the reflectors 50a serves as a channel of the detector 13.

When an X-ray becomes incident on a specific channel of the detector 13, a photoelectric conversion, which is a reaction between the element making up the scintillator 50 and the X-ray, takes place, and a part of the X-ray energy is output again as a fluorescent X-ray. The remaining energy reacts with the scintillator 50, and is turned into scintillation light (visible light). At this time, the fluorescent X-ray may pass through the reflector 50a, and enters another channel (e.g., an adjacent channel), as illustrated in FIG. 5. Hereinafter, this phenomenon is referred to as "escape", to distinguish from fluorescence which will be described later. When the escape occurs, the X-ray having entered another channel will not be detected as a photon count in the specific channel.

When an X-ray becomes incident on a channel nearby the specific channel in the detector 13, the X-ray reacts with the element making up the scintillator 50, in the same manner as described above, and emits fluorescent light resultant of the photoelectric effect. At this time, the fluorescent light may pass through the reflector 50a via the nearby channel, as illustrated in FIG. 5, and enter the specific channel. Hereinafter, this phenomenon is simply referred to as "fluorescence", to distinguish from the escape described above. When the fluorescence occurs, a part of the energy of the X-ray incident on the other channel is detected at the specific channel.

In addition to the photoelectric conversion, an X-ray incident on the scintillator 50 may go through Compton scattering or Rayleigh scattering (hereinafter, simply referred to as "scattering") when the X-ray collides with the element making up the scintillator 50. The X-ray, having the traveling direction inflected, may pass through the reflector 50a via a channel positioned near the specific channel, as illustrated in FIG. 5, and may enter the specific channel. This scattering will cause the energy of the X-ray incident on another channel to be detected partly or entirely at the specific channel.

The energy of an X-ray incident on the scintillator 50 reacts partly or entirely with the scintillator 50, and is converted into scintillation light. Although the scintillation light is reflected on the reflectors 50a, as mentioned earlier, if the reflectors 50a are not provided in a manner extending into the adhesive layer 51 as illustrated in FIG. 5, the scintillation light generated at a channel near the specific channel may pass through the adhesive layer 51, and may be detected at the specific channel of the SiPM 52. Hereinafter, this phenomenon is referred to as "cross-talk". When the cross-talk occurs, the photons of the energy of an X-ray that is incident on another channel and should be detected at that channel are partly detected at the specific channel.

Due to the effect of the escape, the fluorescence, the scattering, and the cross-talk described above, the detector 13 detects an incident spectrum 2001 that is a spectrum of X-rays passed through the subject 40 and being incident on a specific channel of the detector 13 as a spectrum having a waveform of the detected spectrum 2011 as illustrated in FIG. 6. The detected spectrum 2011 is represented as a sum of the spectrum of X-rays being incident on the specific channel and having its entire energy detected by the SiPM 52 corresponding to the specific channel, and the spectrums 2012 to 2014, as illustrated in FIG. 6. The spectrum 2012 represents a spectrum of X-rays a part of the energy of which has moved to another channel due to the escape, and the remaining energy of which is detected at the specific channel. The spectrum 2013 represents a spectrum of X-rays that are incident on another channel, but a part of the energy of which is detected at the specific channel because of fluorescence. The spectrum 2014 represents a spectrum of X-rays that are incident on another channel, but a part of the energy of which is detected at the specific channel because of cross-talk and scattering. In other words, the detected spectrum 2011 represents a spectrum with a distorted waveform with respect to the incident spectrum 2001 that is the exact waveform that should be detected by the detector 13. The image processor 34 in the X-ray examination apparatus 1 according to the embodiment, therefore, performs an operation for bringing the detected spectrum 2011, which is a distorted waveform, closer to the waveform of the incident spectrum 2001, through a correction which will be described later. A configuration and an operation of the image processor 34 will now be explained in detail.

Explained herein is an example in which the detector 13 is what is called an indirect conversion detector, as illustrated in FIG. 5, but embodiments are not limited thereto, and the detector 13 may be a direct conversion detector that detects the X-rays directly without scintillator. In a direct conversion detector as well, physical phenomena with similar effects as escape, fluorescence, cross-talk, and scattering described above may take place as the X-rays pass through a material making up the detector.

Figure 7:
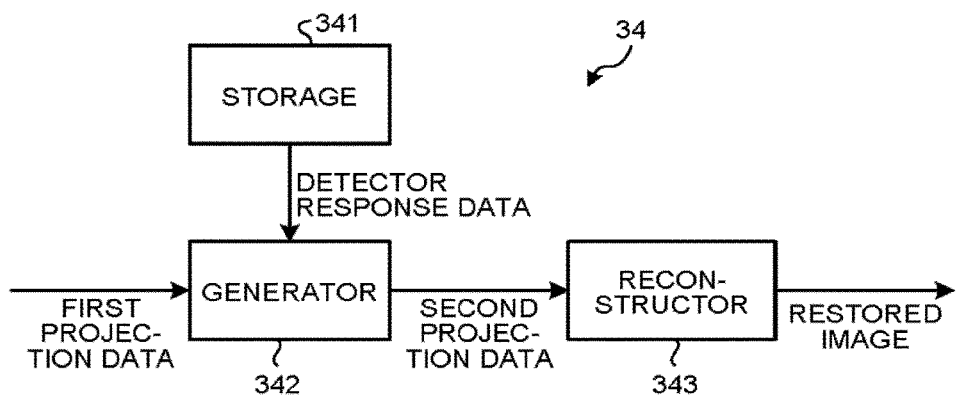
FIG. 7 is a schematic illustrating an exemplary block diagram of an image processor according to the first embodiment.

FIG. 7 is a schematic illustrating an exemplary block diagram of the image processor according to the first embodiment. The block diagram of the image processor 34 according to the embodiment will now be explained with reference to FIG. 7.

As illustrated in FIG. 7, the image processor 34 includes a storage 341, a generator 342, and a reconstructor 343.

The storage 341 is a functional unit that stores therein detector response data (response information) which will be described later. The storage 341 is not limited to the configuration provided to the image processor 34, but the image storage 35 illustrated in FIG. 1 may serve as the storage 341, as an example.

The generator 342 is a functional unit that receives subject sinograms that are sinograms of the subject 40 as first projection data from the data collector 16, reads the detector response data from the storage 341, and generates second projection data in a sinogram format based on the first projection data and the detector response data. The first projection data is data consisting of a set of subject sinograms (first sinograms) each of which corresponds to an energy band having a predetermined width, and is generated by the data collector 16 based on the spectrums of photon counts in units of the energy detected by the detector 13 at each view and each channel. The second projection data has the same data format as the first projection data, and is a data consisting of a set of subject sinograms (second sinograms) each of which corresponds to an energy band having the predetermined width. Hereinafter, data having the same data format as the first projection data and the second projection data is sometimes simply referred to as "projection data". In the explanation below, it is assumed that the first projection data and the second projection data are both sets of 140 subject sinograms each of which has pixel values representing photon counts in the corresponding energy band (a first energy band and a second energy band) that is at an increment of 1 [keV] across the spectrum of photon counts of energy ranging from 0 [keV] to 140 [keV]. In other words, the 140 subject sinograms represent photon counts corresponding to energy bands of 0 [keV] to 1 [keV], 1 [keV] to 2 [keV], . . . , and 139 [keV] to 140 [keV], respectively.

Specifically, to generate the second projection data, the generator 342 calculates the second projection data by correcting the distortion in the first projection data using the first projection data and the detector response data with Expression (1) below.

$$\underset{x_p}{\mathrm{argmin}} \left\| y_p - \left( M x_p + \sum_{i \in N} C_i x_i \right) \right\|^2 \text{ for } \forall\, p \quad (1)$$

where p denotes a pixel in the subject sinograms making up the first projection data and the second projection data; $y_p$ denotes the data representing the first projection data on which the generator 342 performs an operation, and specifically, is a 140-dimensional vector of pixel values (photon counts) at the pixel p across the entire subject sinograms making up the first projection data; and $x_p$ denotes the data representing the second projection data generated by the generator 342, and specifically, is a 140-dimensional vector of pixel values (photon counts) at the pixel p across the entire subject sinograms making up the second projection data. M is a 140×140 matrix representing the energy response of a specific channel of the detector 13 (the channel corresponding to the pixel p) detecting the X-rays being incident on the specific channel. The energy response M includes the spectrum of X-rays having the entire energy detected by the specific channel, a spectrum of X-rays having the energy detected by the specific channel due to escape, a spectrum of X-rays having the energy detected by the specific channel due to scattering, and the like. The j-column component of M represents the spectrum of the response to a range of X-ray energy of (j−1) [keV] to j [keV], among the entire energy band of X-rays incident on the specific channel of the detector 13.

In Expression (1), $x_i$ represents a 140-dimensional vector consisting of pixel values (photon counts) at a pixel i positioned near the pixel p in the subject sinograms making up the second projection data; and $C_i$ is data representing a response spectrum detected by the specific channel due to the fluorescence, the cross-talk, and the scattering, among the X-rays incident on the channel corresponding to the pixel i, which is nearby the specific channel (the channel corresponding to the pixel p) in the detector 13, and is a matrix of 140 by 140. The j-column components of $C_i$ represents an energy band of (j−1) [keV] to j [keV], in the entire range of the X-rays energy incident on the channel corresponding to the pixel i in the detector 13, and is a response spectrum detected when the specific channel (the channel corresponding to the pixel p) detects X-rays. In Expression (1), N denotes a set of pixels within a predetermined area (an area in the channel direction and the slice direction) near the pixel p, at the same view as the pixel p, and the pixel i is included in the set N.

The matrix M and matrix $C_i$ will be explained below, assuming that all of the pixels in the subject sinograms making up the first projection data and the second projection data are constant. The matrix M and the matrix $C_i$ may be set to each pixel of the subject sinograms based on specific variability or the like resulting from a production error in the detector 13. For example, the matrix M and the matrix $C_i$ may be set by measuring the response characteristic and the variability specific to each channel of the detector 13 in advance.

The detector response data herein is data representing the degree by which physical phenomena contribute to an error in the spectrum that is to be output as a response characteristic of the detector 13 on which the X-rays are incident. The detector response data is, as an example, data based on at least one of the following factors: a probability at which the escape occurs in the specific channel, information of the spectrum of X-ray energy originating from a nearby channel but detected at the specific channel due to fluorescence, cross-talk, scattering, and the like, and the dispersion of detected energy, in units of the X-ray energy being incident on the specific channel of the detector 13. Specifically, the detector response data represents data of the matrix M and the matrix $C_i$ in Expression (1). In other words, the detector response data is data for correcting the first projection data, and generating the second projection data, as described above.

In other words, the generator 342 generates projection data from which projection data that is closer to the first projection data can be acquired by taking a change in the spectrum introduced by the detector response data into consideration as indicated by Expression (1) above, as the second projection data.

In Expression (1) above, the proximity between the first projection data and the projection data resultant of taking a change in the spectrum introduced by the detector response into consideration is defined as an L2 norm of a vector, but the proximity calculation is not limited thereto, and any distance defined between vectors may be used. For example, Lp norm such as L1 norm, L2 norm, or L∞ norm may be used. Furthermore, the norm may be calculated by weighting each component. Furthermore, a distance considering a correlation between vector components, such as Mahalanobis' distance, may also be used.

Furthermore, the width of the energy band used in the first projection data and the second projection data is not limited to 1 [keV], and the units of the energy is not limited to [keV]. Furthermore, the energy band of the spectrum is not also limited to 0 [keV] to 140 [keV]. In other words, the energy band may have a different width, or the unit of the energy may be a different unit such as [J] or [cal]. Furthermore, the unit of the first projection data and the second projection data is not limited to the unit of energy. For example, the first projection data may be in units of the digital signal read from the detector 13, and the second projection data may be in units of [keV].

Furthermore, the first projection data and the second projection data are explained to be a set of 140 subject sinograms the pixel value of which represents a photon count in each of the 140 energy bands of the spectrum of photon counts across the entire energy band of 0 [keV] to 140 [keV], but there is no limitation for the numbers of energy bands in the first projection data and the second projection data to be the same. For example, the first projection data may be a set of 28 subject sinograms with a pixel value representing a photon count in units of an energy band at an increment of 5 [keV](first energy band), and the second projection data may be a set of 140 subject sinograms with a pixel value representing a photon count in units of an energy band at an increment of 1 [keV](second energy band), for the energy of 0 [keV] to 140 [keV]. In such a case, the difference in the number of energy bands in the first projection data and the second projection data may be resolved by setting the dimension of the matrix M and the matrix $C_i$ as 28×140. At this time, as the $j^{th}$ row components of the matrix M and the matrix $C_i$ may be the additions of the components in $(5×j+1)^{th}$ row to the $(5×j+5)^{th}$ row across each column in the 140×140 matrix M and matrix $C_i$.

When the generator 342 actually calculates the second projection data using the Expression (1) above, the generator 342 makes the calculation through the iteration expressed by Equation (2) below.

$$x_p^{(k+1)} = \underset{x_p}{\operatorname{argmin}} \left\| y_p - \left( M x_p + \sum_{i \in N} C_i x_i^{(k)} \right) \right\|^2 \text{ for } \forall\, p \quad (2)$$

The generator 342, to begin with, sets some initial value of the second projection data in Equation (2). For example, the generator 342 may use the first projection data as the initial value of the second projection data. Once $(k+1)^{th}$ iteration is completed, the generator 342 uses $x_p^{(k+1)}$ as the second projection data to use $x_p^{(k+1)}$ as $x_i^{(k)}$ in calculating Equation (2) for the following update. The iteration may be repeated by a predetermined number of times, for example, and stopped when the difference between the second projection data calculated from Equation (2) and the second projection data immediately previously calculated from Equation (2) becomes equal to or less than a predetermined threshold.

The detector response data may change depending on the number of X-ray photons being incident on the detector 13 per unit time. For example, when X-ray photons become incident on the detector 13 successively, the response of the detector 13 may become insufficient, and the detector 13 may detect a photon count representing X-ray energy lower than the actual energy. To address this issue, the generator 342 may generate second projection data by switching pieces of detector response data depending on the photon count of the first projection data. In such a case, the counts of photons being incident on the detector 13 per unit time may be classified into 10 different levels, and the detector response data corresponding to the respective levels may be stored in the storage 341. The generator 342 then calculates the photon count for each pixel of the subject sinograms making up the first projection data, reads the detector response data corresponding to the photon count from the storage 341, and uses the detector response data. The generator 342 may also synthesize and read the pieces of detector response data that are close to the photon count at the corresponding pixel of the subject sinograms making up the first projection data. Let us assume herein that, for example, the storage 341 stores therein $M_{500}$ and $C_{i,500}$ that are detector response data corresponding to a photon count of "500", and $M_{1000}$ and $C_{i,1000}$ that are detector response data corresponding to a photon count of "1000". Under this condition, if the photon count of the corresponding pixel of the subject sinograms making up the first projection data is "700", the generator 342 calculates a weighted average of these pieces of detector response data, based on the proximity of the photon count "700" to the photon count "500", and the proximity of the photon count "700" to the photon count of "1000". In other words, the generator 342 calculates $(3/5)M_{500}+(2/5)M_{1000}$, and, $(3/5)C_{i,500}+(2/5)C_{i,1000}$ as the detector response data before reading the data. The storage 341 may also store therein a coefficient for correcting a change in the detector response data due to the change in the photon count, and the generator 342 may adjust the coefficient based on the photon count of the corresponding pixel in the subject sinograms making up the first projection data, and adjusts the detector response data with the coefficient before reading the detector response data. Assuming that the incident spectrum of the X-rays passed through the subject 40 and being incident on the specific channel of the detector 13 is sufficient approximation of the incident spectrum of the X-rays incident on a channel that are spatially and temporally near the specific channel, the data from the nearby channel may be synthesized with the data from the specific channel, so that the result can be used as the first projection data. An exemplary way of synthesizing, a weighted average may be used. A channel at a spatial proximity to the corresponding pixel in the sinograms making up the first projection data is a nearby channel in the channel direction and the slice direction. A channel at a temporal proximity is data from a nearby view, or data from a different view just by 360 degrees in the projection data collected by rotating the detector twice or more. In this manner, highly accurate second projection data can be generated even when the first projection data cannot be observed highly accurately due to a low dose and photon fluctuation.

The reconstructor 343 is a functional unit that generates a restored image by reconstructing a subject sinogram corresponding to the energy band to be restored, among the subject sinograms included in the second projection data generated by the generator 342. A restored image is an image in which a pixel value represents a linear attenuation coefficient, for example. As a reconstruction method, for example, filtered back projection (FBP) that is an example of back project may be used. Explained herein is an example in which an image is reconstructed from a subject sinogram of the second projection data with FBP. In this example, it is assumed that the reconstructor 343 is provided with reference data $I_0$ that is an air sinogram generated from the part of the spectrum corresponding to the energy band to be restored of X-rays only passed through the air, without passing through the subject 40, and detected by the detector 13. Among the subject sinograms included in the second projection data, the subject sinogram representative of the energy band to be restored is referred to as data to be restored I. The data to be restored I is calculated as a sum of photon counts corresponding to the energy belonging to the energy band to be restored in the second projection data.

The reconstructor 343, to begin with, calculates an integral M of the linear attenuation coefficients from the data to be restored I and the reference data $I_0$, based on Equation (3) below.

$$M(m, n) = -\log\frac{I(m, n)}{I_0(m, n)} \quad (3)$$

where (m, n) denotes data at the $m^{th}$ channel and the $n^{th}$ view. The integral M(m, n) denotes an integral of the linear attenuation coefficients of the subject 40, the integral being taken along a path of the X-rays emitted from the X-ray tube 11 and reaching the $m^{th}$ channel of the detector 13 at the $n^{th}$ view.

The reconstructor 343 then performs one-dimensional Fourier transform to the calculated integral M(m, n) in the channel direction. The reconstructor 343 then applies filtering in the frequency direction, with a high-pass filter such as ramp filter or the Shepp-Logan filter to the results of the one-dimensional Fourier transform, and performs one-dimensional inverse Fourier transform. The reconstructor 343 then generates a restored image that is a reconstructed reconstruction image, by applying back projection to the data resultant of the one-dimensional inverse Fourier transform at each view.

Explained above is an example in which the reconstructor 343 reconstructs a restored image using FBP that is an example of back projection, but the reconstruction method is not limited to FBP, and various other reconstruction methods such as iterative reconstruction may be used. For example, iterative reconstruction is a method in which an attenuation ratio is calculated from an artificial tentative image prepared in advance, and a subject is then irradiated with X-rays from the tube at each view. When the attenuation ratio calculated with the tentative image is smaller than the actual measurement (attenuation ratio) detected by the detector 13, the pixel values of the tentative image are increased. By contrast, when the attenuation ratio calculated with the tentative image is larger than the actual measurement (attenuation ratio) detected by the detector 13, the pixel values of the tentative image are decreased. A reconstruction image is acquired by repeating this operation until the attenuation ratio calculated with the tentative image becomes equal to the actual measurement (attenuation ratio) detected by the detector 13. There are many variations of the iterative reconstruction such as algebraic reconstruction technique (ART), ordered subset expectation maximization (OS-EM), and maximum likelihood expectation maximization (ML-EM).

Figure 8:
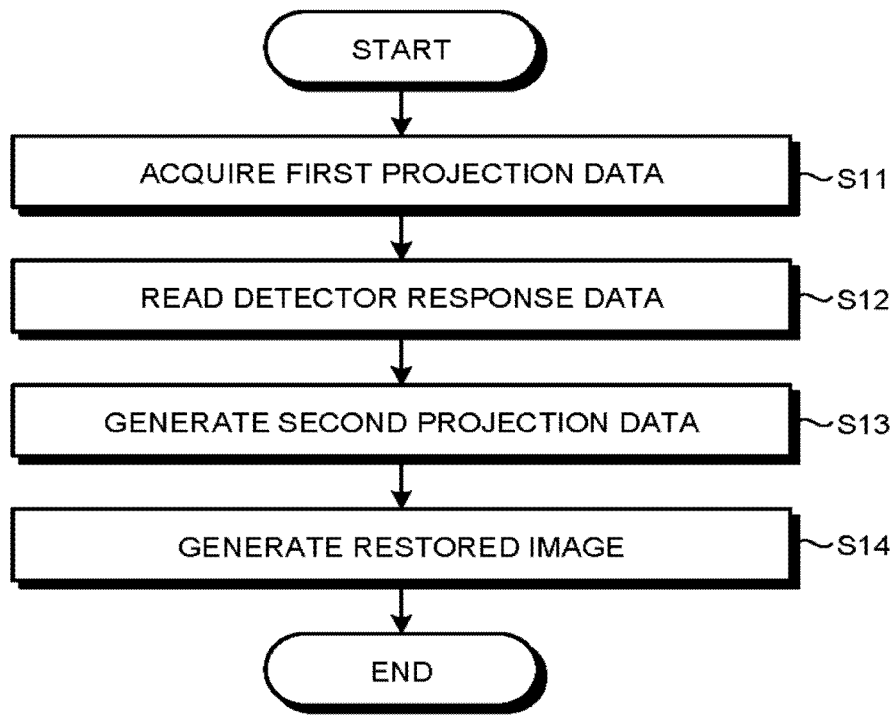
FIG. 8 is a flowchart illustrating an exemplary operation of the image processor according to the first embodiment.

FIG. 8 is a flowchart illustrating an exemplary operation of the image processor according to the first embodiment. The image processing operation performed by the image processor 34 according to the embodiment will now be explained with reference to FIG. 8.

Step S11

The generator 342 in the image processor 34 receives to acquire subject sinograms that are sinograms of the subject 40 from the data collector 16 as the first projection data.

The process is then shifted to Step S12.

Step S12 The generator 342 reads to acquire the detector response data from the storage 341 in the image processor 34. The process is then shifted to Step S13.

Step S13

The generator 342 generates the second projection data with distortion in the first projection data corrected from the acquired first projection data and detector response data using Expression (1) above. The detector response data is data of the matrix M and the matrix $C_i$ in Expression (1) above. The generator 342 generates the projection data that is closer to the first projection data with the effect of the detector response data applied, as the second projection data, as indicated by Expression (1) above. The generator 342 then sends the generated second projection data to the reconstructor 343 in the image processor 34. The process is then shifted to Step S14.

Step S14

The reconstructor 343 reconstructs a restored image from the subject sinogram corresponding to the energy band to be restored, among the subject sinograms included in the second projection data generated by the generator 342. Specifically, the reconstructor 343 calculates, to begin with, an integral M(m, n) of the linear attenuation coefficients from the data to be restored I that is the subject sinogram of the energy band to be restored, among the subject sinograms included in the second projection data, and the reference data $I_0$ with the Equation (3). The reconstructor 343 then performs the one-dimensional Fourier transform to the calculated integral M(m, n) in the channel direction. The reconstructor 343 then applies filtering with a high-pass filter such as ramp filter or the Shepp-Logan filter to the results of the one-dimensional Fourier transform in the frequency direction, and performs one-dimensional inverse Fourier transform. The reconstructor 343 then generates a restored image that is a reconstructed reconstruction image by applying back projection to the data resultant of the one-dimensional inverse Fourier transform at each view.

The image processor 34 performs the image processing through the operation from Step S11 to Step S14.

As described above, the generator 342 calculates the second projection data resulting from correcting the distortion in the first projection data using detector response data, such as a probability at which the escape occurs in the specific channel, information of the spectrum of the X-ray energy originating from a nearby channel but detected at the specific channel due to fluorescence, cross-talk, scattering, and the like, in the units of X-ray energy incident on the specific channel of the detector 13. In other words, the generator 342 generates projection data for bringing the projection data applied with the effect of detector response data closer to the first projection data, as indicated by Expression (1) above, as the second projection data. The reconstructor 343 then generates a restored image by reconstructing the subject sinogram corresponding to the energy band to be restored, among the subject sinograms included in the second projection data generated by the generator 342. In this manner, a pixel value in subject sinograms each of which corresponds to a predetermined energy band can be corrected to be closer to the theoretical values (first projection data), regardless of the composition of the subject, so that the correction accuracy of the X-ray spectrum detected by the detector 13 can be improved, and the exactness of the eventually reconstructed restored image can be improved. For example, a restored spectrum recovered from each of the subject sinograms included in the second projection data (hereinafter, simply referred to as a "restored spectrum of the second projection data") can be brought closer to the shape of the X-ray spectrum passed through the subject 40 and being incident on the detector 13 (incident spectrum).

In the description above, the detector 13 is explained to detect a spectrum of photon counts in units of the energy at each of the channels (each of the detecting elements) arranged in the circumferential direction of the rotating frame 12. The detecting elements of the detector 13 are, however, also arranged in the rostrocaudal direction of the subject 40. The sinograms may therefore be generated for each of the ring-like arrangements of the detecting elements that are arranged in the rostrocaudal direction (slice direction), and the image processing described above may be performed to such sinograms. In an example in which the rotating frame 12 is rotated continuously while moving the couch top 22 as in the helical scan, the sinograms may be generated by interpolating the data detected by the channels (the detecting elements) arranged along the same circumferential direction with the data detected by the channels offset in the rostrocaudal direction (slice direction). Furthermore, it is also possible to enable the X-ray tube 11 to emit X-rays at two different energy levels, and to switch the energy level every time the rotating frame 12 is rotated once (e.g., 140 [keV] in the first rotation, and 80 [keV] in the second rotation), as in a dual-energy X-ray CT apparatus, and to generate sinograms from the synthesis of these energy spectrums.

The pixel values of the restored image generated by the reconstructor 343 are explained to be linear attenuation coefficients, but any values such as CT values representative of the degree by which X-rays attenuate may be used effectively as the pixel values without limitation. In the same manner, the pixel values of the sinograms may be any values indicating the amount of X-ray, such as the amount of X-ray itself, values indicating the quantities of photon count, or any ratio indicating a change in the amount of X-ray or the photon count.

First Modification

An image processor 34a according to a first modification of the first embodiment will now be explained, focusing on the difference with the image processor 34 according to the first embodiment. The image processor 34a according to the first modification includes a storage 341a and a generator 342a, which will be described later, illustrated in FIG. 9, instead of the storage 341 and the generator 342 provided to the image processor 34 illustrated in FIG. 7 according to the first embodiment.

Figure 9:
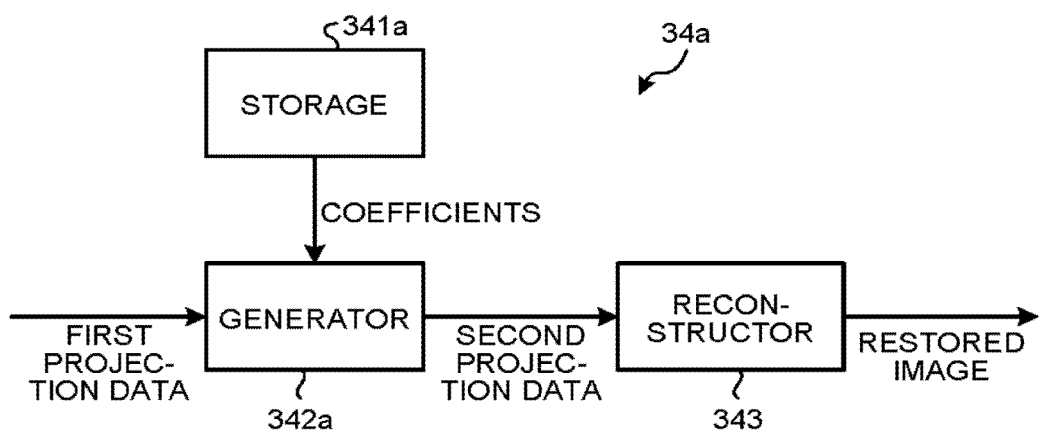
FIG. 9 is a schematic illustrating an exemplary block diagram of an image processor according to a first modification of the first embodiment.
Figure 10:
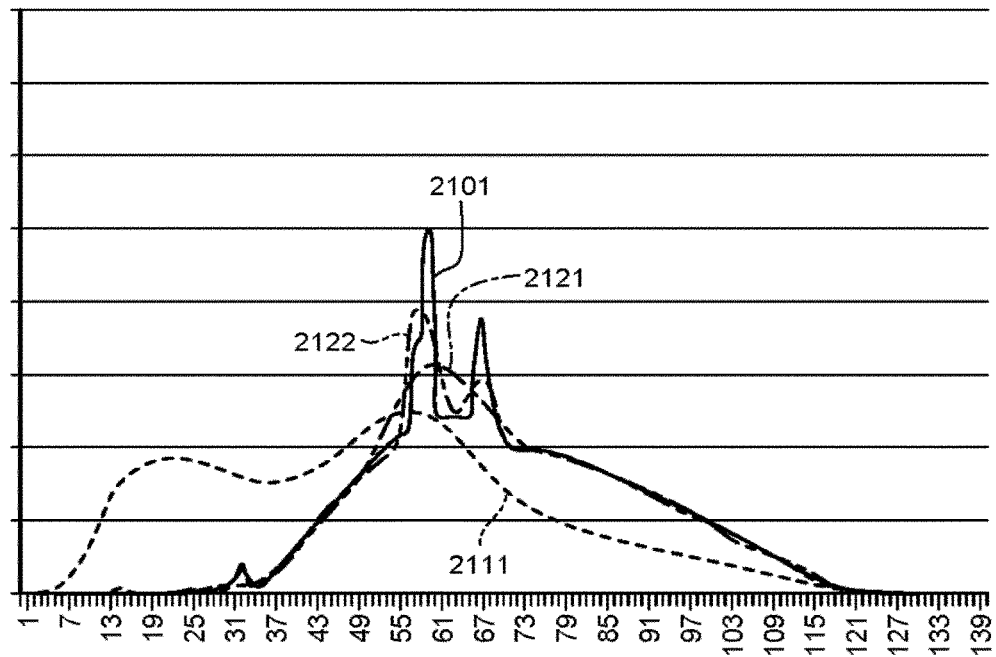
FIG. 10 is a schematic illustrating an exemplary restored spectrum resultant of correcting the detected spectrum.

FIG. 9 is a schematic illustrating an exemplary block diagram of the image processor according to the first modification of the first embodiment. FIG. 10 is a schematic illustrating an exemplary restored spectrum resultant of correcting the detected spectrum. A block diagram and an operation of the image processor 34a according to the modification will now be explained with reference to FIG. 9.

As illustrated in FIG. 9, the image processor 34a includes the storage 341a, the generator 342a, and the reconstructor 343.

The storage 341a is a functional unit that stores therein filter coefficients for converting the first projection data into the second projection data, as will be described later.

The generator 342a is a functional unit that receives the subject sinograms that are sinogram of the subject 40 from the data collector 16, as the first projection data, reads the filter coefficients for converting the first projection data into the second projection data from the storage 341a, and generates the second projection data in the sinogram format based on the first projection data and the filter coefficients. It is assumed herein that an incident spectrum of X-rays passed through the subject 40 and being incident on a specific channel of the detector 13 is a sufficient approximation of an incident spectrum of X-rays being incident on another channel that is spatially near the specific channel. In such case, Expression (1) above can be substituted with Expression (4) below.

$$\operatorname*{argmin}_{x_p} \|y_p - Hx_p\|^2 \text{ for } \forall\, p \qquad (4)$$

where H is a 140×140 matrix expressed by Equation (5) below.

$$H = M + \sum_{i \in N} C_i \quad (5)$$

The generator 342a is capable of calculating the second projection data with distortion in the first projection data corrected with Expression (4) above, using the first projection data and data of the matrix H (corresponding to the detector response data described above). To ensure the tolerance against noise and detection error of the detector 13, however, a regularization term λf (information indicating continuity) is added to the value indicated in Expression (4), as indicated Expression (6) below.

$$\operatorname*{argmin}_{x_p}\{\|y_p - Hx_p\|^2 + \lambda f(x_p)\} \text{ for } \forall\, p \quad (6)$$

where λ is a weight indicating the regularization intensity, and $f(x_p)$ is a function indicating smoothness (continuity) of the spectrum of $x_p$ in the energy direction. The function f(x) is expressed as, for example, Equation (7) below.

$$f(x) = \sum_{j=1,2,\ldots,139} (x(j+1) - x(j))^2 \quad (7)$$

The function f(x) may also be expressed as Equation (8) below.

$$f(x) = \sum_{j=1,2,\ldots,139} |x(j+1) - x(j)|^2 \quad (8)$$

In Equation (7) and Equation (8), x(j) denotes the $j^{th}$ component (photon count) of x; f(x) is a function outputting a greater value when the difference between adjacent components (photon count) is greater.

Expression (6) above can be solved with an iterative algorithm such as the gradient method or the subgradient method. Furthermore, when the function f(x) is the function expressed in Equation (7), Expression (6) can be solved analytically. Explained below is this example.

When function f(x) is the function expressed in Equation (7), Expression (6) is equivalent to Expression (9) below.

$$\operatorname*{argmin}_{x_p} \|y'_p - Sx_p\|^2 \text{ for } \forall\, p \quad (9)$$

where S is a matrix of (140+139)×140 expressed as Equation (10) below.

$$S = \begin{pmatrix} & H & & \\ -\lambda & \lambda & & 0 \\ & -\lambda & \lambda & \\ & & \ddots & \\ 0 & & -\lambda & \lambda \end{pmatrix} \quad (10)$$

In Equation (9), $y'_p$ is a (140+139) dimensional vector expressed as Equation (11) below.

$$y'_p = (y_p^T, 0, 0, \ldots, 0)^T \quad (11)$$

Here, $x_p$ which is the solution of Expression (9) can be calculated with Equation (12) below using a pseudo inverse matrix $S^+$ of the matrix S. The pseudo inverse matrix $S^+$ can be calculated with the singular value decomposition of the matrix S.

$$x_p = S^+ y'_p \quad (12)$$

The filter coefficients stored the storage 341a are the values of the components of the pseudo inverse matrix $S^+$. The generator 342a generates the second projection data with distortion in the first projection data corrected, by convoluting the first projection data with the filter coefficients read from the storage 341a, as expressed in Equation (12). In other words, because the filter coefficients stored in the storage 341a are data for correcting the first projection data and generating the second projection data, the filter coefficients can be considered as the detector response data.

The reconstructor 343 is a functional unit that generates a restored image by reconstructing the subject sinogram corresponding to an energy band to be restored, among the subject sinograms included in the second projection data generated by the generator 342a. The reconstructor 343 operates reconstruction process to the subject sinogram following the same method as that according to the first embodiment.

Let us assume herein that the X-rays passed through the subject 40 and represented by the incident spectrum 2101 illustrated in FIG. 10 become incident on a specific channel of the detector 13. In such a case, the spectrum detected by the detector 13 will be distorted, as in a distorted detected spectrum 2111, due to escape, fluorescence, cross-talk, scattering, and the like, with respect to the incident spectrum 2101. The data collector 16 applies processes such as amplification and A/D conversion to each piece of spectrum data collected from the detector 13 (an example of which is the detected spectrum 2111), generates sinograms corresponding to respective energy bands having a predetermined width, and sends the sinograms to the generator 342a as the first projection data. The spectrum recovered by the generator 342a from the subject sinograms in the second projection data calculated using Equation (12) taking the regularization term expressed in Expression (6) into account is the restored spectrum 2121 illustrated in FIG. 10. In the manner described above, by causing the generator 342a to calculate the second projection data using Equation (12) that takes the regularization term, which is expressed as Expression (6), into account, the restored spectrum 2121 can be approximated to a shape closer to the incident spectrum 2101, compared with the detected spectrum 2111. Furthermore, because the generator 342a can generate the second projection data using simplified Equation (12), computational load can be reduced.

Explained above is an example in which the storage 341a stores therein the values of the components of the pseudo matrix $S^+$ expressed in Equation (12) as the coefficients, and the generator 342a generates the second projection data by convoluting the first projection data with the filter coefficients read from the storage 341a as expressed in Equation (12), but embodiments and modifications are not limited thereto. For example, the storage 341a may store therein the matrix H and the weight λ as the detector response data, instead of storing the coefficients that are the values of the components of the pseudo matrix $S^+$. In such a case, the generator 342a can generate the second projection data by calculating Expression (6), Equations (7) to (8), Expression (9), and Equations (10) to (12) using the detector response data stored in the storage 341a.

Second Modification

An operation of the reconstructor 343 according to a second modification of the first embodiment will now be explained, focusing on the difference with the reconstructor 343 according to the first embodiment. The reconstructor 343 according to the second modification estimates the density of a specific substance based on the linear attenuation coefficients represented in the pixels of a reconstructed restored image and the mass attenuation coefficient of the specific substance. The operation of estimating the substance density will now be explained in detail.

The reconstructor 343 in the image processor 34 according to the second modification generates a plurality of restored images in which linear attenuation coefficients are represented as pixel values, by operating reconstruction process to subject sinograms corresponding to a plurality of respective energy bands, instead of operating reconstruction process to a subject sinogram corresponding to a target energy band, among those included in the second projection data, as in the first embodiment. Explained herein is an example in which substance densities are estimated when water and iodine are the substances included in the subject 40.

To begin with, the reconstructor 343 generates two restored images in which the linear attenuation coefficients are represented as pixel values by operating reconstruction process to the subject sinograms corresponding to a specific energy band (e.g., 35 to 50 [keV]), and the subject sinograms corresponding to an energy band that is different from the specific energy band (e.g., 55 to 70 [keV]) (second energy band), among the subject sinograms included in the second projection data. The reconstructor 343 then calculates the substance density at each pixel of the restored images, based on the simultaneous equations indicated as Equations (13).

$$\left. \begin{array}{l} \rho_w(s,t) v_{w,1} + \rho_I(s,t) v_{I,1} = \mu_1(s,t) \\ \rho_w(s,t) v_{w,2} + \rho_I(s,t) v_{I,2} = \mu_2(s,t) \end{array} \right\} \quad (13)$$

where (s, t) denotes coordinates in a restored image; $\rho_w$ and $\rho_I$ denote the substance densities of water and iodine, respectively, and are values to be calculated from Equations (13); $v_{w,1}$ and $v_{I,1}$ are the mass attenuation coefficients of water and iodine, respectively, within the specific energy band, and these values are known; $v_{w,2}$ and $v_{I,2}$ denote the mass attenuation coefficients of water and iodine, respectively, within the range that is different from the specific energy band, and these values are also known; $\mu_1$ denotes a pixel value representing a linear attenuation coefficient in the restored image reconstructed from the subject sinogram corresponding to the specific energy band by the reconstructor 343; and $\mu_2$ denotes a pixel value representing a linear attenuation coefficient in the restored image reconstructed from the subject sinogram corresponding to the energy band that is different from the specific energy band by the reconstructor 343. Because $v_{w,1}$, $v_{I,1}$, $v_{w,2}$, and $v_{I,2}$ are known, and $\mu_1$ and $\mu_2$ are already determined, Equations (13) can be said to be simultaneous equations for $\rho_w$ and $\rho_I$. The reconstructor 343 can, therefore, obtain $\rho_w$ and $\rho_I$ at each pixel (coordinate (s, t)) of the restored images, by solving Equations (13) that are simultaneous equations for $\rho_w$ and $\rho_I$. The reconstructor 343 can then generate density images of water and iodine by replacing the pixel value at each pixel of the respective restored images with the substance densities $\rho_w$ and $\rho_I$, respectively, at the corresponding pixel.

As described above, because the reconstructor 343 generates a restored image representing linear attenuation coefficients with improved accuracy, the reconstructor 343 can generate a density image presenting a more accurate density of a specific substance in the subject 40 from the restored image.

Furthermore, explained above is an example in which acquired are the densities of water and iodine, but the substance the density of which is acquired is not limited to water and iodine. The reconstructor 343 may also generate a density image of any other substance such as bone or gadolinium. Furthermore, in the example described above, the densities of two different substances which are water and iodine are acquired, but the number of substances is not limited to two, and the densities of three or more substances may also be acquired. In such a case, the reconstructor 343 may generate restored images in which the linear attenuation coefficients are represented as pixel values from the subject sinograms corresponding to the energy bands in a number equal to or more than the number of substances the densities of which are calculated.

It is also possible to generate a tomographic image in which substance densities are represented as pixel values by performing the reconstruction after the substance density at each pixel of the sinogram is estimated, instead of by estimating the density of the substance after the reconstruction image is generated.

A method for computing substance density images of water and iodine will now be explained, as an example. To begin with, the reconstructor 343 calculates a sum of the energy values in the subject sinograms belonging to a specific energy band (e.g., 35 to 50 [keV]) (hereinafter, referred to as an energy band A), among the subject sinograms included in the second projection data, and a sum of the energy values in the subject sinograms belonging to an energy band that is different from the specific energy band (e.g., 55 to 70 [keV]) (hereinafter, referred to as an energy band B) (which are denoted by $I_1$ and $I_2$, respectively). In the same manner, the reconstructor 343 calculates a sum of the values in the air sinograms belonging to the energy band A and a sum of the values in those belonging to the energy band B (which are denoted by $I_{0,1}$ and $I_{0,2}$, respectively).

The reconstructor 343 then calculates integrals M1 and M2 of the linear attenuation coefficients in the respective energy bands, from Equation (14).

$$M_1(m,n) = -\log\frac{I_1(m,n)}{I_{0,1}(m,n)}, \ M_2(m,n) = -\log\frac{I_2(m,n)}{I_{0,2}(m,n)} \quad (14)$$

The reconstructor 343 then calculates the transmittance distances of the respective substances at each pixel of the sinograms, from the simultaneous equations indicated as Equations (15).

$$\begin{array}{l} l_w(m,n) z_{w,1} + l_I(m,n) z_{I,1} = M_1(m,n) \\ l_w(m,n) z_{w,2} + l_I(m,n) z_{I,2} = M_2(m,n) \end{array} \quad (15)$$

where $l_w$ and $l_I$ denote the distances of the water and the iodine, respectively, that are found along the transmission path of the X-ray, with regard to the pixel (m, n) in the sinograms, and these are values to be obtained; $z_{w,1}$ and $z_{I,1}$ are linear attenuation coefficients of the water and the iodine, respectively, in the energy band A; and $z_{w,2}$ and $z_{I,2}$ are linear attenuation coefficients of the water and the iodine, respectively, in the energy band B. Once operating reconstruction process to $l_w$ and $l_I$ using FBP, for example, a tomographic image representing the water density and another tomographic image representing the iodine density can be generated by multiplying the water density with $l_w$, and the iodine density with $l_I$. Explained above is an example in which the substances are water and iodine, but the substances are not limited to water and iodine. It is also possible to calculate the substance densities of three or more substances. In such a case, energy bands in a number greater than the number of substances should be created, and simultaneous equations in a number greater than the number of the substances should be provided.

Second Embodiment

An image processor 34b according to a second embodiment will now be explained, focusing on the difference with the image processor 34a according to the first modification of the first embodiment. The image processor 34b according to the embodiment calculates the function f(x), which is indicated in Equation (7), for example, in the regularization term λf in Expression (6), by giving a weight depending on the difference between a pixel value (photon count) of an energy band and the corresponding pixel value in an adjacent energy band. The calculating operation with such a weight will now be explained in detail.

Figure 11:
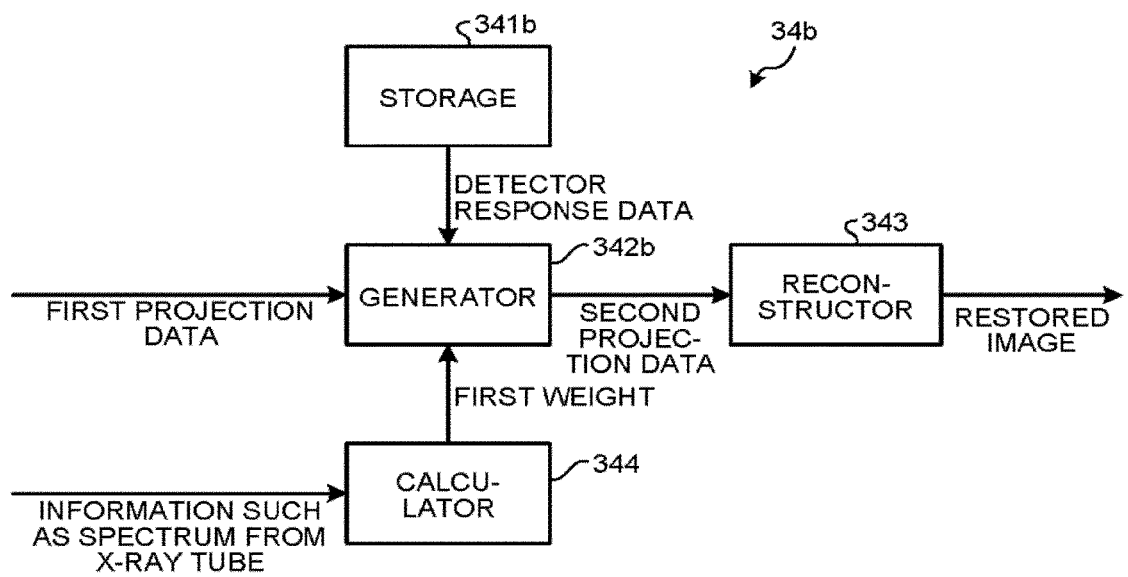
FIG. 11 is a schematic illustrating an exemplary block diagram of an image processor according to a second embodiment.

FIG. 11 is a schematic illustrating an exemplary block diagram of the image processor according to the second embodiment. In FIG. 12, (a) illustrates an exemplary outgoing spectrum of the X-rays emitted from the X-ray tube, and (b) illustrates an exemplary subject spectrum. A block diagram of the image processor 34b according to the embodiment will now be explained with reference to FIG. 11.

As illustrated in FIG. 11, the image processor 34b includes a storage 341b, a generator 342b, the reconstructor 343, and a calculator 344.

The storage 341b is a functional unit that stores therein the matrix H and the weight λ expressed in Expression (6) above as the detector response data.

The generator 342b is a functional unit that receives the subject sinograms that are sinograms of the subject 40 from the data collector 16 as the first projection data, reads the detector response data from the storage 341b, and generates the second projection data in the sinogram format based on the first projection data and the detector response data. It is also assumed herein that the incident spectrum of X-rays passed through the subject 40 being incident on a specific channel of the detector 13 is a sufficient approximation of the incident spectrum of X-rays being incident on a channel positioned near the specific channel, in the same manner as in the first modification of the first embodiment.

Expression (6) above is addition of the regularization term λf to Expression (4) above. In the embodiment, the function f(x) in the regularization term λf is calculated by multiplying a first weight $w_j$ to the difference between a pixel value (photon count) of an energy band and the corresponding pixel in an adjacent energy band, as expressed in Equation (16) below.

$$f(x) = \sum_{j=1,2,\ldots,139} (w_j(x(j+1) - x(j)))^2 \tag{16}$$

Alternatively, the function f(x) may be expressed as Equation (17) below.

$$f(x) = \sum_{j=1,2,\ldots,139} w_j |x(j+1) - x(j)| \tag{17}$$

When the function f(x) is expressed as Equation (16) above, Expression (6) above is equivalent to Expression (18) below.

$$\operatorname*{argmin}_{x_p} \|y'_p - WSx_p\|^2 \text{ for } \forall p \tag{18}$$

where W is a matrix of (140+139)×(140+139) expressed as Equation (19) below.

$$W = \operatorname{diag}(1,1,\ldots,1,w_1,w_2,\ldots,w_{139}) \tag{19}$$

Here, $x_p$, which is the solution of Expression (18) above, can be calculated with Equation (20) below using a pseudo inverse matrix $(WS)^+$ of the matrix WS that is a matrix of (140+139)×140. The pseudo inverse matrix $(WS)^+$ can be calculated by the singular value decomposition of the matrix S.

$$x_p = (WS)^+ y_p \tag{20}$$

The generator 342b calculates to generate the second projection data with distortion in the first projection data corrected from the first weight $w_j$ calculated by the calculator 344, which will be described later, and the detector response data (matrix H, weight λ) read from the storage 341b, based on Expression (6), Equation (16), Expression (18), and Equations (19) to (20).

The reconstructor 343 is a functional unit that reconstructs a restored image from a subject sinogram corresponding to an energy band to be restored, among the subject sinograms included in the second projection data generated by the generator 342b. The reconstructor 343 operates reconstruction process to the subject sinogram following the same method as that according to the first embodiment.

The calculator 344 is a functional unit that calculates the first weight $w_j$ expressed by Equation (16) above so as to allow the generator 342b to calculate the second projection data. The calculator 344 acquires the degree by which the restored spectrum of the second projection data is expected to change sharply in the energy direction based on information of at least one of information of the outgoing spectrum that is a spectrum of X-rays emitted from the X-ray tube 11, the target member of the X-ray tube 11, the angle of the target in the X-ray tube 11, the filter in the X-ray tube 11, the tube voltage of the X-ray tube 11 used when images are being captured, a contrast agent used, and the expected composition of the subject 40, for example, and calculates the first weight $w_j$. The calculator 344 calculates the first weight $w_j$ in such a manner that a smaller first weight $w_j$ is applied at an energy level where the restored spectrum of the second projection data is expected to change sharply in the energy direction, and a greater weight $w_j$ is applied at an energy level where the restored spectrum is expected to change smoothly in the energy direction. The calculator 344 can acquire the information such as the information of the outgoing spectrum that is a spectrum of X-rays emitted from the X-ray tube 11, the target member of the X-ray tube 11, the angle of the target in the X-ray tube 11, the filter in the X-ray tube 11, the tube voltage of the X-ray tube 11 used when images are being captured, the contrast agent used, and the expected composition of the subject 40 from the system controller 36, for example.

A specific example of how the first weight $w_j$ is calculated by the calculator 344 will now be explained with reference to FIG. 12. The calculator 344 acquires information of an outgoing spectrum 2200, one example of which is illustrated in (a) in FIG. 12, that is the spectrum of X-rays emitted from the X-ray tube 11 from the system controller 36, for example. The calculator 344 then detects that the spectrum changes sharply in the energy direction at the part corresponding to energy levels E1 and E2, based on the form of the outgoing spectrum 2200, and calculates the first weight $w_j$ in such a manner that a smaller first weight $w_j$ is applied near the energy levels E1 and E2. For example, the calculator 344 sets the first weight $w_j$ to "1" in ranges of energy level E1±3 [keV] and E2±3 [keV], and sets the first weight $w_j$ to "10" in the remaining energy bands. The first weight $w_j$ is set in this manner because a sharp change in the energy direction in the outgoing spectrum 2200 will result in a sharp change in the energy direction at the same energy levels in a spectrum of the X-rays passed through the subject 40.

The form of the outgoing spectrum of the X-rays emitted from the X-ray tube 11 can be calculated from the information such as the target member of the X-ray tube 11, the angle of the target in the X-ray tube 11, the filter in the X-ray tube 11, and the tube voltage of the X-ray tube 11 used when images are being captured, without acquiring the information of the form directly, and therefore, the result of such calculations may also be used. Furthermore, the information of an energy level at which the outgoing spectrum of the X-rays emitted from the X-ray tube 11 changes sharply in the energy direction can be acquired from at least one of information of the target member of the X-ray tube 11, the angle of the target in the X-ray tube 11, the filter in the X-ray tube 11, and the tube voltage of the X-ray tube 11 used when images are being captured, without calculating the form of the outgoing spectrum.

When a contrast agent such as iodine or gadolinium is included in the subject 40, the subject spectrum that is a spectrum of the X-rays attenuated by passing through the subject 40 (which can also be considered as an incident spectrum in a sense that the X-rays become incident on the detector 13) changes sharply in the energy direction at the energy level of the K absorption edge of the contrast agent.

In FIG. 12, (b) illustrates a subject spectrum 2201 as an exemplary spectrum of the X-rays attenuated through the subject 40 including iodine as the contrast agent. The subject spectrum 2201 illustrated in (b) in FIG. 12 exhibits a sharp change at an energy level E3. The calculator 344 therefore detects that the spectrum changes sharply in the energy direction at the part corresponding to the energy level E3 based on the form of the subject spectrum 2201, and calculates the first weight $w_j$ in such a manner that a smaller first weight $w_j$ is applied at the energy near the energy level E3. The calculator 344 sets, for example, the first weight $w_j$ to "1" in the energy band E3±3 [keV], in addition to the energy bands E1±3 [keV] and E2±3 [keV], and sets the first weight $w_j$ to "10" in the remaining energy bands. The energy at the K absorption edge is a value unique to the contrast agent, and the K absorption edge of iodine is at 33 [keV], and the K absorption edge of gadolinium is at 50 [keV].

It is preferable to cause the calculator 344 to calculate the first weight $w_j$ based on the information of the contrast agent when the contrast agent is included in the subject 40. When it is not clear whether the contrast agent is present, the calculator 344 may calculate the first weight $w_j$ based on the contrast agent that may be used. Furthermore, the calculator 344 may receive the information of the contrast agent used from the system controller 36 or the like. Furthermore, a user may input the information of the contrast agent used via the input device 31. It is also possible to allow a user to input the value of an energy level at which the second projection data is expected to change sharply in the energy direction directly via the input device 31.

As described above, the generator 342b generates the second projection data using the first weight $w_j$ calculated by the calculator 344. In other words, the generator 342b generates the projection data that is closer to the first projection data with the effect of the detector response data applied as the second projection data, by functioning to increase the smoothness in the energy direction at the energy level where a greater first weight $w_j$ is applied, and to reduce the function of increasing the smoothness in the energy direction at the energy where a smaller first weight $w_j$ is applied.

Let us assume herein that X-rays passed through the subject 40 and represented by the incident spectrum 2101 illustrated in FIG. 10 become incident on a specific channel of the detector 13. In such a case, the spectrum detected by the detector 13 will be a distorted detected spectrum 2111 due to escape, fluorescence, cross-talk, scattering, and the like, with respect to the incident spectrum 2101. The data collector 16 applies processes such as amplification and A/D conversion to each piece of spectrum data collected from the detector 13 (an example of which is the detected spectrum 2111), generates a sinogram corresponding to each unit of the energy having a predetermined width, and sends the sinograms to the generator 342b as the first projection data. The spectrum recovered by the generator 342b from the spectrum of the subject sinograms in the second projection data that is calculated with Equation (20) taking the regularization term and the first weight $w_j$ expressed in Expression (6) above into consideration is the restored spectrum 2122 illustrated in FIG. 10. In the manner described above, by causing the generator 342a to calculate the second projection data using Equation (20) that takes the regularization term and the first weight $w_j$ into consideration, the part of the restored spectrum 2122 changing sharply in the energy direction can be brought closer to the incident spectrum 2101, compared with the detected spectrum 2111.

The generator 342b may also generate the second projection data by further giving a weight, in units of the energy bands, for an error in the spectrum. Denoting a weight for weighting the second projection data based on an error in the spectrum as a second weight $u_j$, the matrix W expressed as Equation (17) above is expressed as Equation (21) below, instead.

$$W = \mathrm{diag}(u_1, u_2, \ldots u_{140}, w_1, w_2, \ldots, w_{139}) \qquad (21)$$

In other words, the generator 342b may calculate to generate the second projection data from the second weight $u_j$, the first weight $w_j$ calculated by the calculator 344, and the detector response data (matrix H, weight $\lambda$) read from the storage 341b, based on Expression (6), and Equations (16), (17), (19), and (21). It is preferable to use a smaller second weight $u_j$ in an energy band where the reliability in the first projection data is low. For example, a low-energy spectrum can be said to be less reliable, because such a spectrum has been affected by noise of the detector 13. Therefore, the second weight $u_j$ is set to "1" in an energy band where the energy level is lower than a predetermined energy level, and the second weight $u_j$ is set to "10" in an energy band where the energy level is higher than the predetermined energy level. An energy band having a low photon count in the first projection data may also be determined to have lower reliability.

It is also possible to calculate the second weight $u_j$, individually for each pixel of the subject sinogram. For example, when a pixel in the subject sinogram represents a low attenuation level of the X-rays passed through the subject 40, the pixel has been less affected by the noise of the detector 13. Therefore, the reliability of pixel value (photon count) remains high even at a low energy level so that a uniform second weight $u_j$ is applied to all of the energy bands at the corresponding pixel. By contrast, when a pixel in the subject sinogram represents a high attenuation level of the X-rays passed through the subject 40, a smaller second weight $u_j$ is applied to the pixel, in consideration of the noise of the detector 13. In the manner described above, the second weight $u_j$ can be adjusted for each pixel of the subject sinograms.

Figure 13:
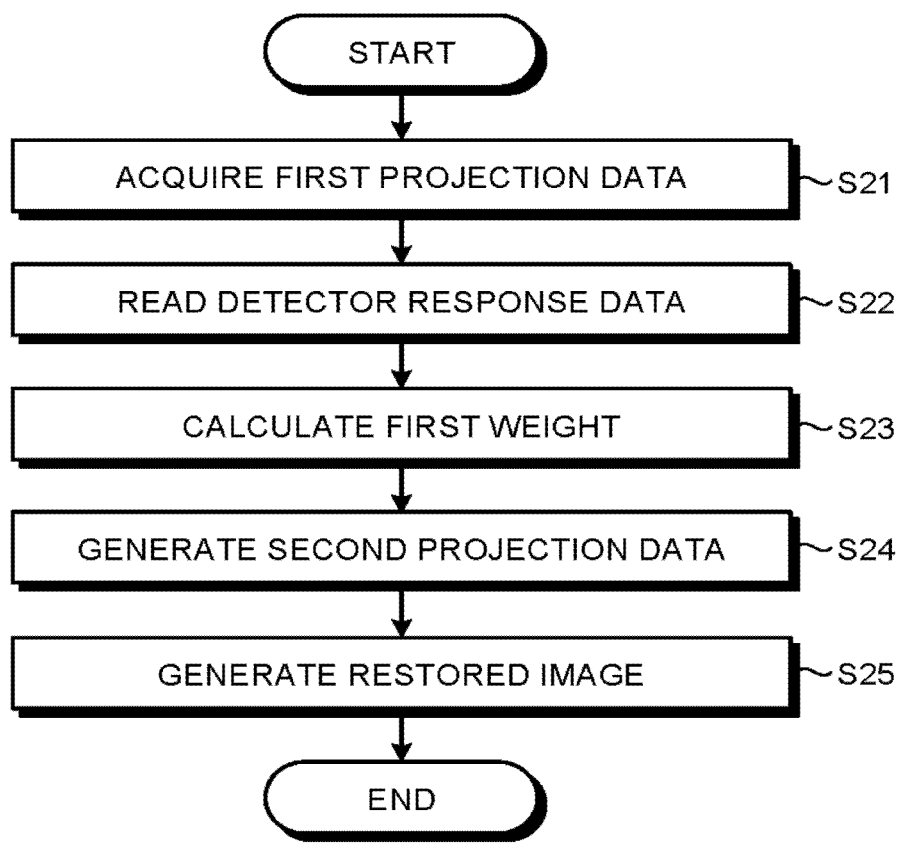
FIG. 13 is a flowchart illustrating an exemplary operation of the image processor according to the second embodiment.

FIG. 13 is a flowchart illustrating an exemplary operation of the image processor according to the second embodiment. The image processing operation performed by the image processor 34*b* according to the embodiment will now be explained with reference to FIG. 13.

Step S21

The generator 342*b* in the image processor 34*b* receives to acquire subject sinograms that are sinograms of the subject 40 from the data collector 16 as the first projection data. The process is then shifted to Step S22.

Step S22

The generator 342*b* reads to acquire the detector response data from the storage 341*b* in the image processor 34*b*. The process is then shifted to Step S23.

Step S23

The calculator 344 calculates the first weight $w_j$ in Equation (16) to be used by the generator 342*b* in calculating the second projection data. To begin with, the calculator 344 acquires at least one of the information of the outgoing spectrum that is a spectrum of X-rays emitted from the X-ray tube 11, the target member of the X-ray tube 11, the angle of the target in the X-ray tube 11, the filter in the X-ray tube 11, the tube voltage of the X-ray tube 11 used when images are being captured, the contrast agent used, and the expected composition of the subject 40, for example, from the system controller 36, for example. The calculator 344 then acquires the degree by which the restored spectrum of the second projection data is expected to change sharply in the energy direction based on the acquired information, and calculates the first weight $w_j$. In other words, the calculator 344 calculates the first weight $w_j$ in such a manner that a smaller first weight $w_j$ is applied at an energy level where the restored spectrum of the second projection data is expected to change sharply in the energy direction, and a greater weight $w_j$ is applied at an energy level where the restored spectrum is expected to change smoothly in the energy direction. The calculator 344 then sends the calculated first weight $w_j$ to the generator 342*b*. The process is then shifted to Step S24.

Step S24

The generator 342*b* then calculates to generate the second projection data with distortion in the first projection data corrected, from the first weight $w_j$ received from the calculator 344, and detector response data, using Equations (6), Equation (16), Expression (18), and Equations (19) to (20). In such a case, the detector response data is the data of the matrix H and the weight λ in Expression (6). The generator 342*b* generates projection data that is closer to the first projection data with the effect of the detector response data applied, as the second projection data. The generator 342*b* then sends the generated second projection data to the reconstructor 343 in the image processor 34. The process is then shifted to Step S25.

Step S25

The reconstructor 343 then reconstructs a restored image from reconstructing the subject sinogram corresponding to the energy band to be restored, among the subject sinograms included in the second projection data generated by the generator 342*b*.

The image processor 34*b* performs the image processing through the operation from Step S21 to S25.

As described above, because the generator 342*a* calculates the second projection data using Equation (20) taking the regularization term and the first weight $w_j$ into consideration, the restored spectrum of the second projection data can be brought closer to the incident spectrum (subject spectrum) even in a part where the spectrum changes sharply in the energy direction, compared with the detected spectrum detected by the detector 13.

Modification

An image processor 34*c* according to a modification of the second embodiment will now be explained, focusing on the difference with the image processor 34*b* according to the second embodiment. An operation of the image processor 34*c* according to the modification will be explained focusing mainly on the operation of the calculator calculating the first weight $w_j$ using the substance density calculated by the reconstructor.

Figure 14:
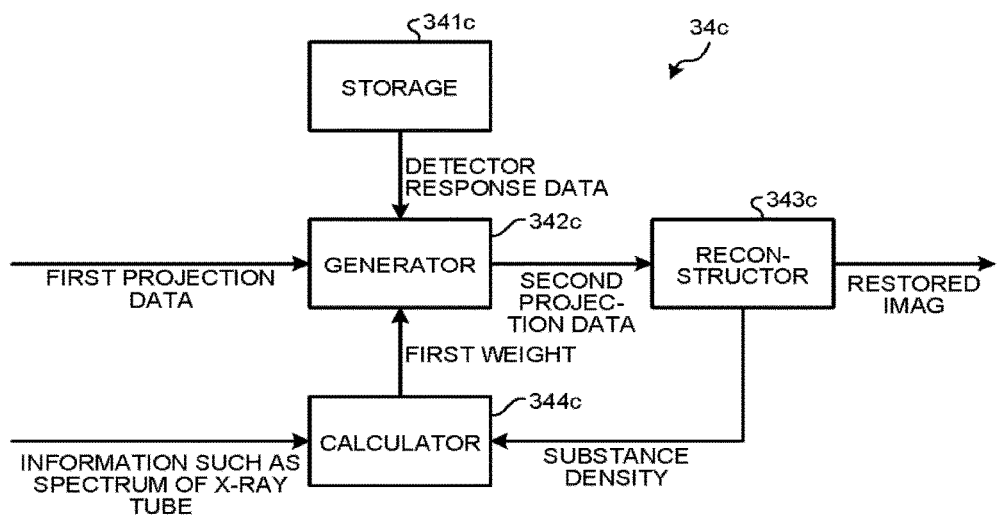
FIG. 14 is a schematic illustrating an exemplary block diagram of the image processor according to a modification of the second embodiment.

FIG. 14 is a schematic illustrating an exemplary block diagram of the image processor according to the modification of the second embodiment. A block diagram and an operation of the image processor 34*c* according to a modification will now be explained with reference to FIG. 14.

As illustrated in FIG. 14, the image processor 34*c* includes a storage 341*c*, a generator 342*c*, a reconstructor 343*c*, and a calculator 344*c*.

The storage 341*c* is a functional unit that stores therein the matrix H and the weight λ expressed in Expression (6) above as the detector response data.

The generator 342*c* is a functional unit that receives the subject sinograms that are sinograms of the subject 40 from the data collector 16 as the first projection data, reads the detector response data from the storage 341*c*, and generates the second projection data in the sinogram format based on the first projection data and the detector response data. The generator 342*c* calculates to generate the second projection data with distortion in the first projection data corrected from the first weight $w_j$ calculated by the calculator 344*c*, which will be described later, and the detector response data (matrix H, weight λ) read from the storage 341*c*, based on Expression (6), Equation (16), Expression (18), and Equations (19) to (20) above.

The calculator 344*c* is a functional unit that calculates the first weight $w_j$ expressed by Equation (16) above to allow the generator 342*c* to calculate the second projection data. The calculator 344*c* acquires the degree by which the restored spectrum of the second projection data is expected to change sharply in the energy direction based on information of at least one of the information of the outgoing spectrum that is a spectrum of X-rays emitted from the X-ray tube 11, the target member of the X-ray tube 11, the angle of the target in the X-ray tube 11, the filter in the X-ray tube 11, the tube voltage of the X-ray tube 11 used when images are being captured, the contrast agent used, and the expected composition of the subject 40, for example, and calculates the first weight $w_j$. The calculator 344*c* also acquires the degree by which the restored spectrum of the second projection data is expected to change sharply in the energy direction based on the substance density calculated by the reconstructor 343c, which will be described later, of a substance included in the subject 40, and calculates the first weight $w_j$.

The reconstructor 343c is a functional unit that reconstructs a restored image from a subject sinogram of the energy band to be restored, among the subject sinogram included in the second projection data generated by the generator 342c. The reconstructor 343c operates reconstruction process to the subject sinogram following the same method as that according to the first embodiment.

The reconstructor 343c identifies, to begin with, substances expected to be included in the subject 40, extracts the subject sinograms corresponding to the energy bands in a number equal to or more than the number of the substances from the second projection data, and generates a plurality of restored images in which the linear attenuation coefficients are represented as the pixel values by operating reconstruction process to the extracted subject sinograms. The reconstructor 343c then calculates the densities of the identified substances at each pixel of the restored images in the same manner as in the second modification of the first embodiment. The reconstructor 343c then sends the information of the calculated substance densities to the calculator 344c.

If the calculator 344c determines that iodine is included in the subject 40 based on the substance densities received from the reconstructor 343c, for example, the calculator 344c calculates the first weight $w_j$ in such a manner that a smaller first weight $w_j$ is applied to the energy levels near 33 [keV]. The generator 342c then generates the second projection data using the first weight $w_j$ calculated by the calculator 344c, in the manner described above. The reconstructor 343c then reconstructs a restored image from the subject sinogram corresponding to the energy band to be restored, among the subject sinogram included in the second projection data generated again by the generator 342c.

The calculator 344c may calculate the first weight $w_j$ correspondingly to the substance density received from the reconstructor 343c. For example, because the restored spectrum of the second projection data will change more in the energy direction when the substance density is high, a smaller first weight $w_j$ may be applied near where the substance density is high.

The calculator 344c may also calculate the first weight $w_j$ individually for each pixel of the subject sinograms. For example, the calculator 344c may receive the substance density from the reconstructor 343c in a format of a density image, and identify the pixels including iodine in the density image. The calculator 344c may then calculate the first weight $w_j$ in such a manner that a smaller first weight $w_j$ is applied near the energy level at the K absorption edge of iodine, only in pixels of the first projection data including these pixels along the transmission path of the X-rays.

As described above, the calculator 344c calculates the first weight $w_j$ based on the substance density calculated by the reconstructor 343c, in addition to the information of the outgoing spectrum that is a spectrum of X-rays emitted from the X-ray tube 11, and the like. Therefore, the restored spectrum of the second projection data can be further brought closer to the form of incident spectrum (subject spectrum) in a part where the spectrum changes sharply in the energy direction, compared with the detected spectrum detected by the detector 13.

Third Embodiment

An image processor according to a third embodiment will now be explained, focusing on the difference with the image processor 34b according to the second embodiment. A generator 342d in the image processor according to the third embodiment generates projection data corresponding to two different spectrums with different degree of smoothness in the energy direction, and synthesizes the projection data. An operation of generating the projection data corresponding to two spectrums, and synthesizing the projection data will now be explained in detail.

Figure 15:
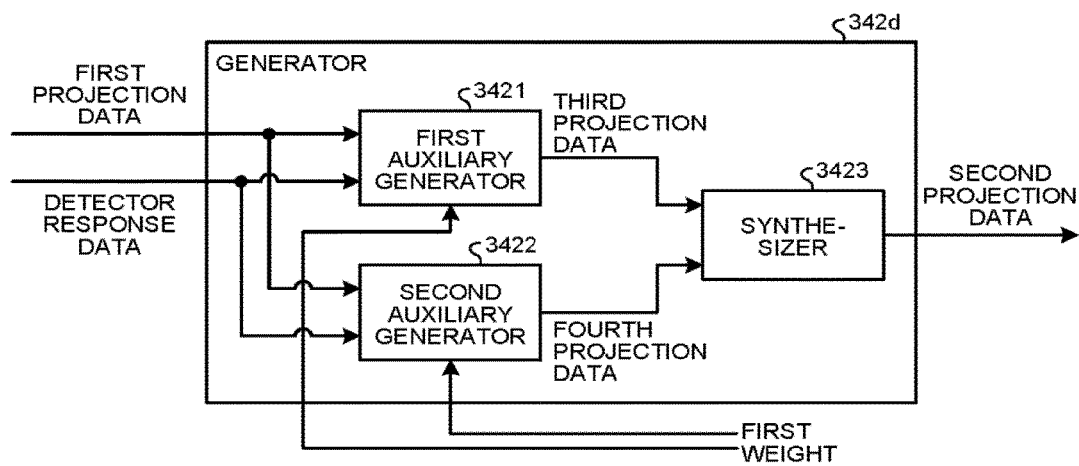
FIG. 15 is a schematic illustrating an exemplary block diagram of a generator in an image processor according to a third embodiment.

FIG. 15 is a schematic illustrating an exemplary block diagram of the generator in the image processor according to the third embodiment. A block diagram of the generator 342d in the image processor according to the embodiment will now be explained with reference to FIG. 15. The image processor according to the embodiment has the same block diagram as that of the image processor 34b according to the second embodiment.

As illustrated in FIG. 15, the generator 342d includes a first auxiliary generator 3421, a second auxiliary generator 3422, and a synthesizer 3423.

The first auxiliary generator 3421 is a functional unit that calculates and generates third projection data with distortion in the first projection data corrected from the first weight $w_j$ calculated by the calculator 344, and the detector response data (matrix H, weight λ) read from the storage 341b, based on Expression (6), Equation (16), Expression (18), and Equations (19) to (20).

The second auxiliary generator 3422 is a functional unit that calculates and generates fourth projection data with distortion in the first projection data corrected, from the first weight $w_j$ calculated by the calculator 344, and the detector response data (matrix H, weight λ) read from the storage 341b, based on Expression (6), Equation (16), Expression (18), and Equations (19) to (20). At this time, the second auxiliary generator 3422 generates the fourth projection data in such a manner that the restored spectrum (fourth spectrum) of the fourth projection data is smoother in the energy direction than the restored spectrum (third spectrum) of the third projection data. In other words, the second auxiliary generator 3422 generates the fourth projection data using a greater first weight in Equation (16) (denoted by $w_j$ in Equation (16)), than that used by the first auxiliary generator 3421 in Equation (16). As an example, the second auxiliary generator 3422 may use a first weight resulting from multiplying a predetermined value that is greater than one to the first weight used by the first auxiliary generator 3421. As another example, a value predefined in such a manner that the first weight used by the second auxiliary generator 3422 is greater than the first weight used by the first auxiliary generator 3421 may also be used.

The synthesizer 3423 is a functional unit that generates the second projection data by synthesizing the third projection data generated by the first auxiliary generator 3421 with the fourth projection data generated by the second auxiliary generator 3422. The synthesizer 3423 applies a greater weight to the third projection data when the first weight $w_j$ received from the calculator 344 is smaller. Specifically, the synthesizer 3423 generates the second projection data using Equation (22) below.

$$x_{p,e} = (1-g_e)x_{p,3,e} + g_e x_{p,4,e} \tag{22}$$

where e is an index indicating the value of the energy band. $x_p$ denotes the data representing the second projection data generated by the synthesizer 3423, and, specifically, is a vector of pixel values (photon counts) at the pixel p across the subject sinograms making up the second projection data; $x_{p,3}$ denotes the data representing the third projection data generated by the first auxiliary generator 3421, and, specifically, is a vector of pixel values (photon counts) at the pixel p across the subject sinograms making up the third projection data; $x_{p,4}$ denotes the data representing the fourth projection data generated by the second auxiliary generator 3422, and, specifically, is a vector of pixel values (photon counts) at the pixel p across the subject sinograms making up the fourth projection data; and g is a weight taking a value from 0 to 1, and is set smaller when the first weight $w_j$ is smaller. For example, a value resulting from dividing the first weight $w_j$ by a predetermined constant and rounding the product to a value equal to or less than one may be used as the weight g.

FIG. 16 is a flowchart illustrating an exemplary operation of the image processor according to the third embodiment. The image processing operation of the image processor according to the embodiment will now be explained with reference to FIG. 16.

Step S31

The generator 342*d* in the image processor receives to acquire subject sinograms that are sinograms of the subject 40 from the data collector 16 as the first projection data. The process is then shifted to Step S32.

Step S32

The generator 342*d* then reads to acquire the detector response data from the storage 341*b* in the image processor. The process is then shifted to Step S33.

Step S33

The calculator 344 then calculates the first weight $w_j$ in Equation (16) above to be used by the generator 342*b* in calculating the second projection data. To begin with, the calculator 344 acquires the information of at least one of the information of the outgoing spectrum that is a spectrum of X-rays emitted from the X-ray tube 11, the target member of the X-ray tube 11, the angle of the target in the X-ray tube 11, the filter in the X-ray tube 11, the tube voltage of the X-ray tube 11 used when images are being captured, the contrast agent used, and the expected composition of the subject 40, for example, from the system controller 36, for example. The calculator 344 then acquires the degree by which the restored spectrum of the second projection data is expected to change sharply in the energy direction based on the acquired information, and calculates the first weight $w_j$. The calculator 344 then sends the calculated first weight $w_j$ to the generator 342*d*.

Step S34

The first auxiliary generator 3421 calculates to generate the third projection data with distortion in the first projection data corrected, from the first weight $w_j$ calculated by the calculator 344, and the detector response data (matrix H, weight λ) read from the storage 341*b*, based on Expression (6), Equation (16), Expression (18), and Equations (19) to (20). The first auxiliary generator 3421 then sends the generated third projection data to the synthesizer 3423. The process is then shifted to Step S35.

Step S35

The second auxiliary generator 3422 is a functional unit that calculates and generates the fourth projection data with distortion in the first projection data corrected, from the first weight $w_j$ calculated by the calculator 344 and the detector response data (matrix H, weight λ) read from the storage 341*b*, based on Expression (6), Equation (16), Expression (18), and Equations (19) to (20). At this time, the second auxiliary generator 3422 generates the fourth projection data in such a manner that the restored spectrum of the fourth projection data is smoother in the energy direction than the restored spectrum of the third projection data. In other words, the second auxiliary generator 3422 generates the fourth projection data, using a greater first weight in Equation (16) (denoted by $w_j$ in Equation (16)), than that to be used by the first auxiliary generator 3421 in Equation (16). The second auxiliary generator 3422 then sends the generated fourth projection data to the synthesizer 3423. The process is then shifted to Step S36.

Step S36

The synthesizer 3423 is a functional unit that generates the second projection data by synthesizing the third projection data generated by the first auxiliary generator 3421 with the fourth projection data generated by the second auxiliary generator 3422. The synthesizer 3423 generates the second projection data using Equation (22) above, by applying a greater weight to the third projection data when the first weight $w_j$ received from the calculator 344 is smaller.

The image processor according to the embodiment performs the image processing through the operation from Step S31 to S36.

As described above, the generator 342*d* generates the second projection data by synthesizing the third projection data having a less smoother restored spectrum in the energy direction, and the fourth projection data having a smoother restored spectrum in the energy direction. In this manner, restored spectrum of the second projection data can be brought closer to the incident spectrum (subject spectrum) even in a part where the spectrum changes sharply in the energy direction, compared with the detected spectrum detected by the detector 13.

The image processing apparatus (the console 30) according to the embodiments and their modifications has a hardware configuration using a general-purpose computer including a micro-processor such as a central processing unit (CPU), a read-only memory (ROM), a random access memory (RAM), an external storage such as a hard disk drive (HDD), a display device such as a display, and an input device such as a keyboard or a mouse.

A computer program executed on the image processing apparatus (the console 30) according to the embodiments and their modifications may be configured to be provided as a computer program product stored in a computer-readable recording medium such as compact disc-read only memory (CD-ROM), a flexible disk (FD), a compact disc recordable (CD-R), and a digital versatile disc (DVD), as a file in an installable or executable format.

The computer program executed on the image processing apparatus (the console 30) according to the embodiments and their modifications may be stored in a computer connected to a network such as the Internet, and be made available for download over the network. The computer program executed on the image processing apparatus (the console 30) according to the embodiments and their modifications may also be provided or distributed over a network such as the Internet.

The computer program executed on the image processing apparatus (the console 30) according to the embodiments and their modifications may be provided in a manner incorporated in a ROM or the like in advance.

The computer program executed on the image processing apparatus (the console 30) according to the embodiments and their modifications can cause a computer to function as the units of the image processing apparatus (the generators 342, 342*a* to 342*d*, the reconstructors 343, 343*c*, the calculators 344, 344*c*, the first auxiliary generator 3421, the second auxiliary generator 3422, and the synthesizer 3423). This computer can cause the CPU to read the computer program from a computer-readable storage medium onto a main memory, and execute the computer program. A part or the whole of the units included in the image processing apparatus may be implemented as a hardware circuit, instead of a computer program that is a piece of software.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus, comprising:
    processing circuitry configured to:
        acquire first projection data that is based on a first spectrum representing an amount of radioactive rays in a unit of energy of the radioactive rays having passed through a subject and detected by a detector;
        generate second projection data by correcting the first projection data based on a response characteristic of the detector; and
        apply a reconstruction process to the second projection data,
    wherein the first projection data is a set of first sinograms that are based on photon counts in a unit of a first energy band in the first spectrum, and
    the second projection data is a set of second sinograms that are based on photon counts in a unit of a second energy band and that are acquired by correction of the first sinograms by the processing circuitry.

2. The apparatus according to claim 1, further comprising:
    an X-ray tube that emits radioactive rays toward the subject; and
    the detector which detects the radioactive rays and outputs the first spectrum,
    wherein the processing circuitry is configured to further collect the first spectrum so as to generate the first projection data.

3. The apparatus according to claim 1, wherein the processing circuitry is configured to further replace the first projection data with data acquired by synthesizing nearby pieces of the first projection data in at least one of a view direction, a channel direction, and a slice direction, to use the acquired data.

4. The apparatus according to claim 1, wherein the response characteristic is information representing a scale of a degree of a physical phenomenon that affects an error in the first spectrum, the scale being output as the response characteristic of the detector on which the radioactive rays are incident.

5. The apparatus according to claim 4, wherein the response characteristic is information that is based on at least one of a probability at which escape occurs in the detector, fluorescence, cross-talk, and scattering affecting a specific channel of the detector from a channel near the specific channel, and dispersion of the energy detected by the detector.

6. The apparatus according to claim 1, wherein the processing circuitry is configured to further switch pieces of the response characteristic to be used in generating the second projection data, based on a photon count in the radioactive rays detected by the detector per unit time.

7. The apparatus according to claim 1, wherein the processing circuitry is configured to further calculate a substance density of a specific substance based on linear attenuation coefficients represented as pixel values in images reconstructed from the second sinograms corresponding to the second energy bands belonging to one or more energy ranges, and a mass attenuation coefficient of the specific substance corresponding to the second energy bands belonging to the one or more energy ranges.

8. The apparatus according to claim 1, wherein the processing circuitry generates the second projection data based on information indicating energy-direction continuity of a second spectrums representing an amount of radioactive rays in a unit of energy based on the second projection data.

9. The apparatus according to claim 8, wherein the processing circuitry is configured to further calculate a first weight for weighting the continuity of a part of the second spectrum corresponding to adjacent second energy bands, wherein
    when the second spectrum exhibits a higher rate of change in an energy direction, the processing circuitry applies a smaller first weight to the second energy bands exhibiting the rate of change.

10. The apparatus according to claim 9, wherein
    the processing circuitry is further configured to calculate the first weight based on at least one of information of a spectrum of radioactive rays emitted from an X-ray tube, a target member of the X-ray tube, an angle of the target in the X-ray tube, a filter in the X-ray tube, a tube voltage supplied to the X-ray tube when images are being captured, a contrast agent used in the subject, and an expected composition of the subject.

11. The apparatus according to claim 9, wherein the processing circuitry is configured to further:
    receive an operation input of information of a contrast agent used in the subject, or information of energy at which the second spectrum is expected to change sharply in an energy direction, and
    calculate the first weight based on the information of the received operation input.

12. The apparatus according to claim 9, wherein the processing circuitry is configured to further:
    calculate a substance density of a specific substance based on a mass attenuation coefficient of the specific substance, and
    calculate the first weight based on the substance density.

13. The apparatus according to claim 8, wherein
    the processing circuitry is configured to further:
        generate third projection data from the first projection data, based on the response characteristic, a first weight, and information indicating energy-direction continuity of a third spectrum representing an amount of radioactive rays in a unit of energy;
        generate fourth projection data from the first projection data, based on the response characteristic, a second weight that is greater than the first weight, and information indicating energy-direction continuity of a fourth spectrum representing an amount of radioactive rays in a unit of energy;
        acquire the second projection data by synthesizing the third projection data and the fourth projection data with a third weight applied to the third projection data and a fourth weight applied to the fourth projection data, wherein the third weight becomes larger as the first weight becomes smaller, and the fourth weight becomes smaller as the first weight becomes smaller.

14. The apparatus according to claim 8, wherein the processing circuitry is further configured to generate the second projection data so that a distance between the first spectrum data and a spectrum generated by transforming the second spectrum with the response characteristic is reduced.

15. The apparatus according to claim 14, wherein the processing circuitry is configured to further calculate a second weight for weighting the distance in a unit of the first energy band, and generate the second projection data using the second weight.

16. The apparatus according to claim 15, wherein the processing circuitry is configured to further calculate a smaller second weight when the energy of the second energy band is smaller.

17. The apparatus according to claim 1, further comprising a memory that stores the response characteristic, wherein
the processing circuitry is configured further to read and acquire the response characteristic from the memory.

18. The apparatus according to claim 17, wherein
the memory stores a filter coefficient for converting the first projection data into the second projection data, as the response characteristic, and
the processing circuitry is further configured to generate the second projection data by reading the filter coefficient from the memory, and by convoluting the first projection data with the filter coefficient.

19. An image processing apparatus, comprising:
a processor; and
a memory that stores processor-executable instructions that, when executed by the processor, cause the processor to:
acquire first projection data that is based on a first spectrum representing an amount of radioactive rays in a unit of energy of the radioactive rays having passed through a subject and detected by a detector;
generate second projection data by correcting the first projection data based on a response characteristic of the detector; and
apply a reconstruction process to the second projection data,
wherein the first projection data is a set of first sinoarams that are based on photon counts in a unit of a first energy band in the first spectrum, and
the second projection data is a set of second sinograms that are based on photon counts in a unit of a second energy band and that are acquired by correction of the first sinograms by the processor.

* * * * *